United States Patent
Corneille et al.

(10) Patent No.: US 9,526,540 B2
(45) Date of Patent: Dec. 27, 2016

(54) INTRAMEDULLARY SYSTEM AND METHOD

(75) Inventors: Patrick R. Corneille, Minneapolis, MN (US); Andreas Carl Pfahnl, Eden Prairie, MN (US); Mark A. McMahan, Highlands Ranch, CO (US); Gary L. Graham, Maple Grove, MN (US); Jeremy J. Ling, St. Paul, MN (US)

(73) Assignee: Distalock, LLC, Eden Prairie, MN (US)

( * ) Notice: Subject to any disclaimer, the term of this patent is extended or adjusted under 35 U.S.C. 154(b) by 148 days.

(21) Appl. No.: 13/505,137

(22) PCT Filed: Nov. 19, 2010

(86) PCT No.: PCT/US2010/057344
§ 371 (c)(1),
(2), (4) Date: Apr. 30, 2012

(87) PCT Pub. No.: WO2011/063184
PCT Pub. Date: May 26, 2011

(65) Prior Publication Data
US 2012/0221005 A1    Aug. 30, 2012

Related U.S. Application Data

(60) Provisional application No. 61/262,878, filed on Nov. 19, 2009, provisional application No. 61/262,865,
(Continued)

(51) Int. Cl.
*A61B 17/72*    (2006.01)
*A61B 17/17*    (2006.01)
(Continued)

(52) U.S. Cl.
CPC .......... *A61B 17/72* (2013.01); *A61B 17/1631* (2013.01); *A61B 17/1633* (2013.01);
(Continued)

(58) Field of Classification Search
CPC . A61B 17/72; A61B 17/7233; A61B 17/7241; A61B 17/725; A61B 17/7283; A61B 17/1725
(Continued)

(56) References Cited

U.S. PATENT DOCUMENTS 4,732,151 A * 3/1988 Jones ................. A61B 17/0643
24/703.4
4,781,181 A * 11/1988 Tanguy ................ A61B 17/164
606/64

(Continued)

FOREIGN PATENT DOCUMENTS

| DE | 40 33 280 A1 | 10/1991 |
| JP | 62-64356 | 3/1987 |
| WO | 99/12485 A1 | 3/1999 |

OTHER PUBLICATIONS

Office Action dated Mar. 28, 2013, issued by the Canadian Patent Office regarding corresponding application Serial No. 2780985, 4 pages.

(Continued)

*Primary Examiner* — Eduardo C Robert
*Assistant Examiner* — Julianna N Harvey
(74) *Attorney, Agent, or Firm* — Kagan Binder, PLLC

(57) ABSTRACT

A system and method for drilling soft tissue and positioning an intramedullary rod in a long bone is provided. The system includes an intramedullary rod having an internal channel sized to provide a tight fit for a drill assembly. The system also includes a step pin used for marking the position of a pilot hole drilled through the bone within which the intramedullary rod is positioned.

8 Claims, 26 Drawing Sheets

Related U.S. Application Data filed on Nov. 19, 2009, provisional application No. 61/262,869, filed on Nov. 19, 2009.

(51) Int. Cl.
*A61B 17/88* (2006.01)
*A61B 17/16* (2006.01)

(52) U.S. Cl.
CPC ...... *A61B 17/1725* (2013.01); *A61B 17/8897* (2013.01); *A61B 17/1615* (2013.01)

(58) Field of Classification Search
USPC .......................................... 606/62–64, 96–98
See application file for complete search history.

(56) References Cited

U.S. PATENT DOCUMENTS

| | | |
|---|---|---|
| 5,374,270 A | 12/1994 | McGuire et al. |
| 6,053,918 A | 4/2000 | Spievack |
| 6,068,642 A | 5/2000 | Johnson et al. |
| 6,428,541 B1 | 8/2002 | Boyd et al. |
| 6,869,434 B2 | 3/2005 | Choi |
| 2003/0229375 A1 | 12/2003 | Fleischer |
| 2006/0095039 A1* | 5/2006 | Mutchler ........................ 606/64 |
| 2007/0049930 A1 | 3/2007 | Hearn et al. |
| 2008/0172125 A1 | 7/2008 | Ek |
| 2009/0104252 A1 | 4/2009 | Alam et al. |
| 2009/0149862 A1 | 6/2009 | Kim |
| 2009/0206127 A1 | 8/2009 | Danielson et al. |

OTHER PUBLICATIONS

International Search Report, dated Jan. 27, 2011, regarding PCT International Patent Application PCT/US2010/057344, 3 pages.

Japanese Office Action, mailed Aug. 12, 2013, regarding corresponding patent application:JP 2012-540074, 5 pages (with English translation), Japanese Patent Office.

* cited by examiner

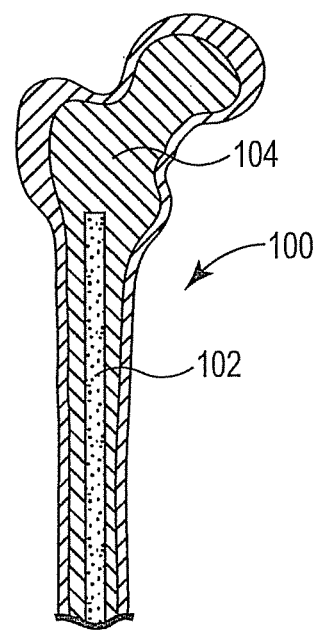
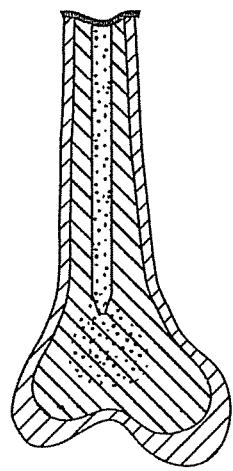
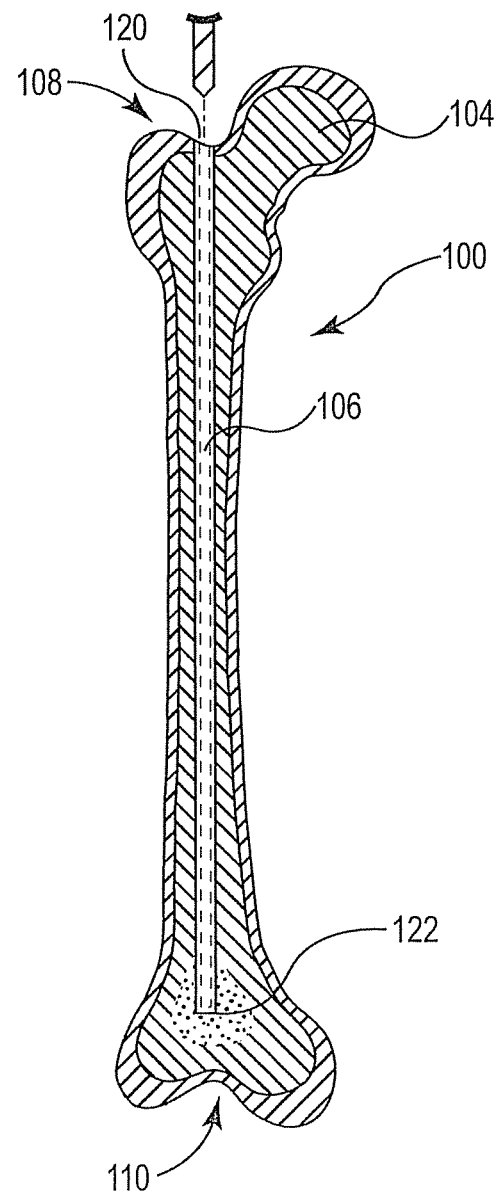
Fig. 1
Fig. 2

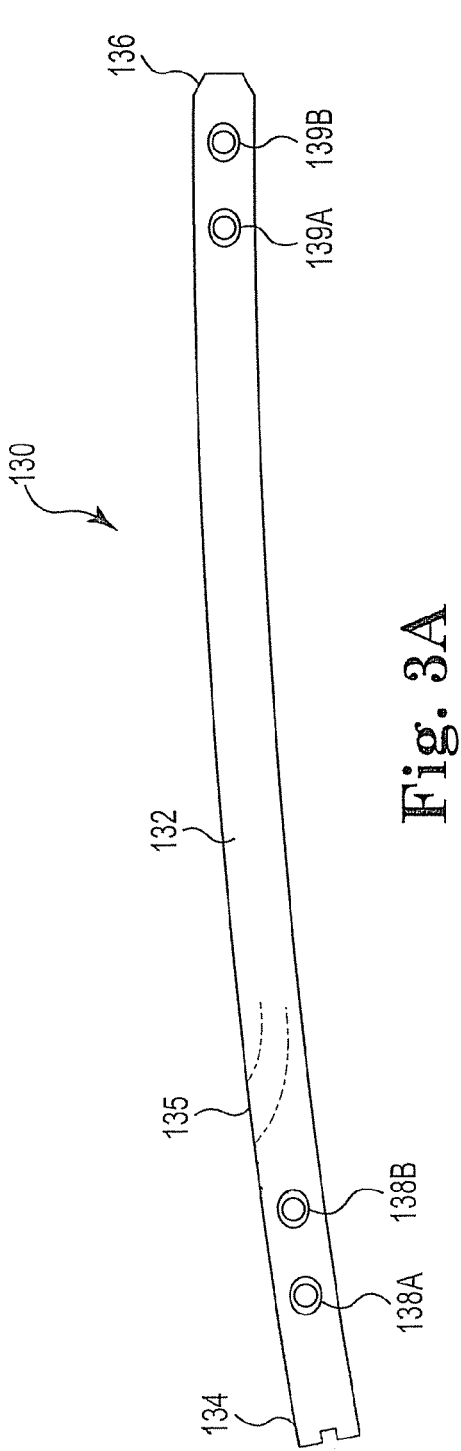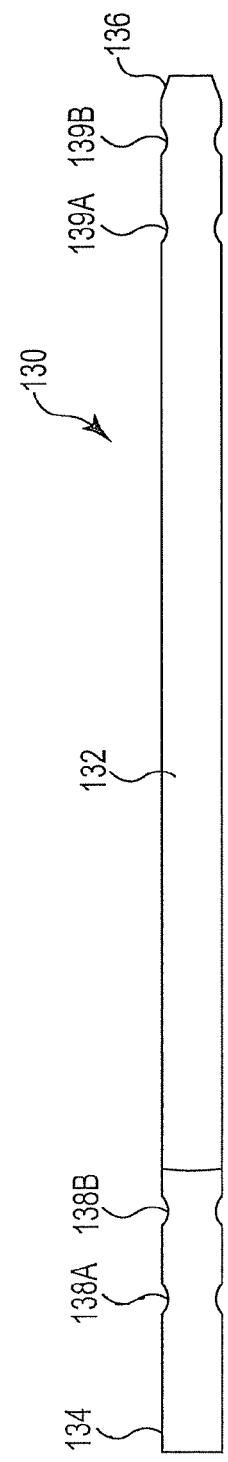

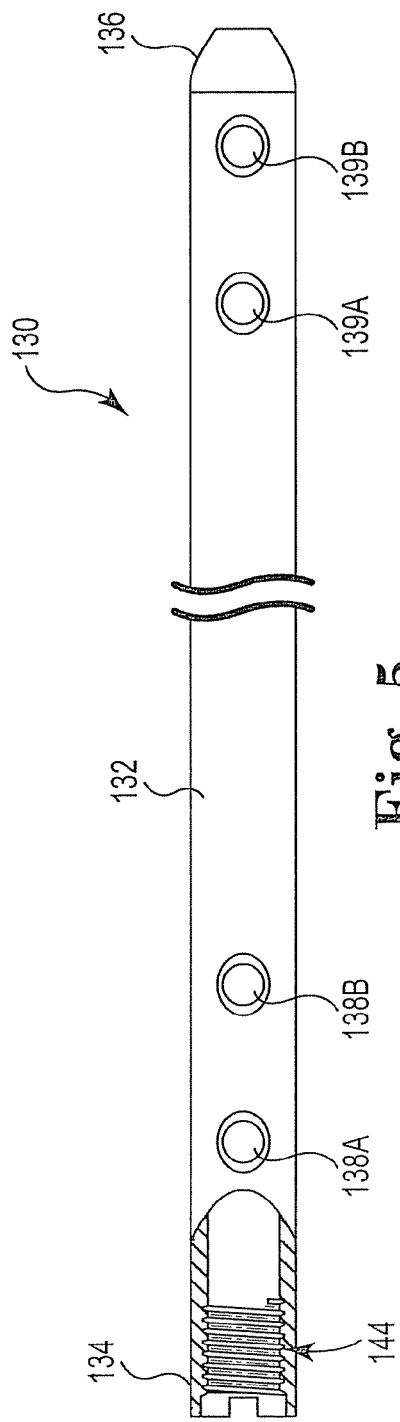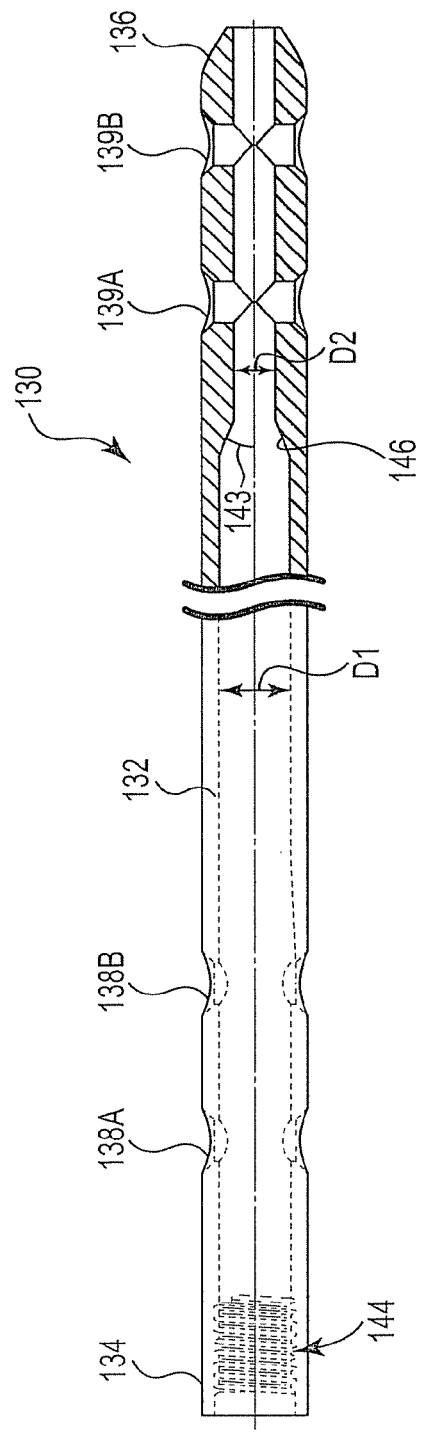

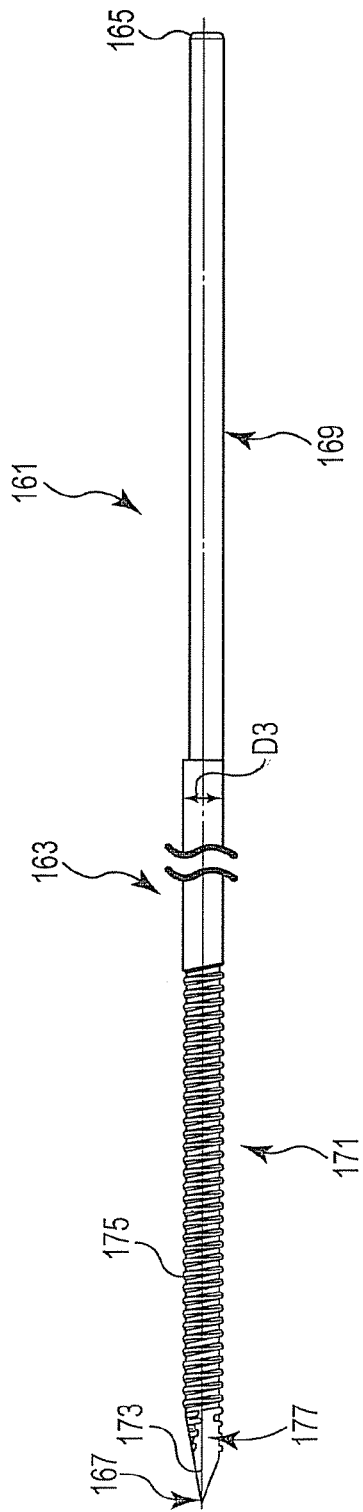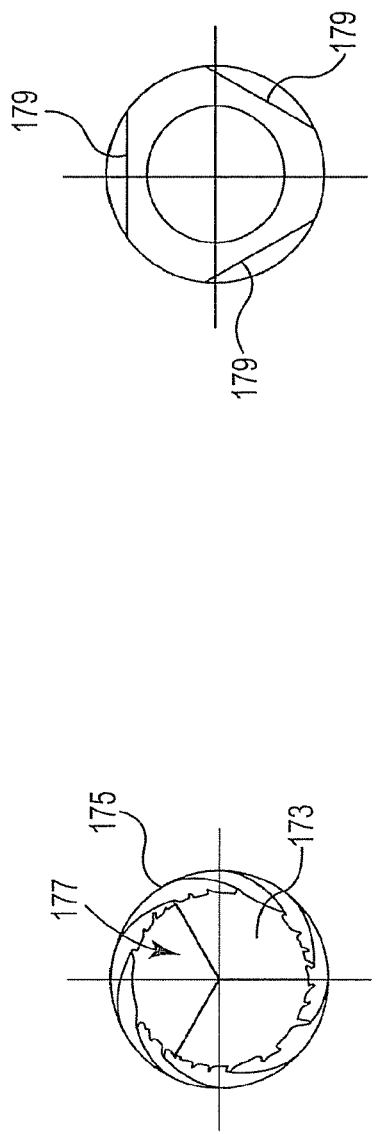

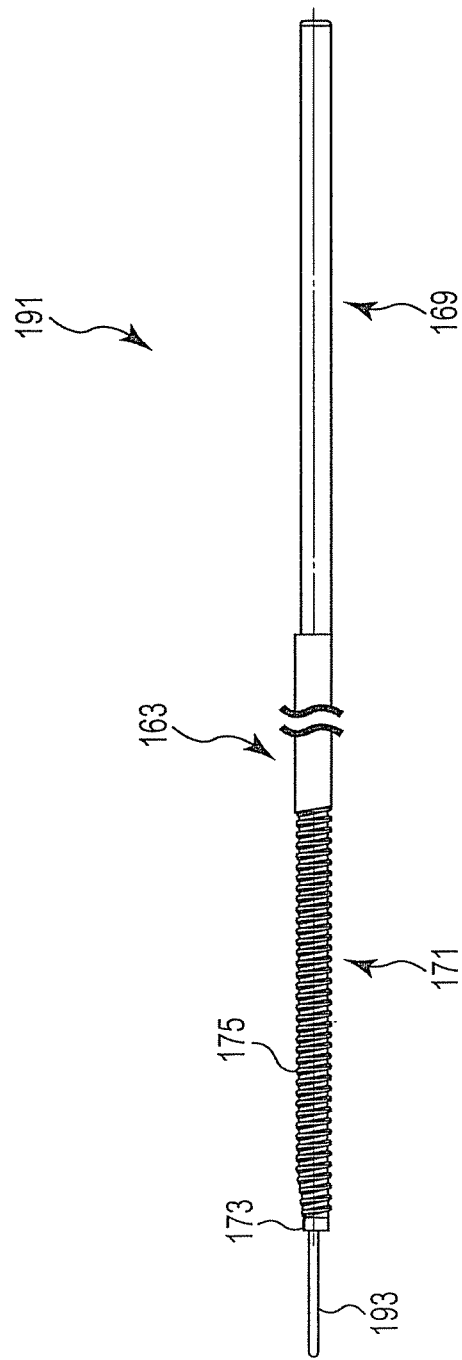

INTRAMEDULLARY SYSTEM AND METHOD

BACKGROUND OF INVENTION

1. Field of Invention

The present invention relates to a system and method for drilling soft tissue and positioning an intramedullary rod in a long bone.

2. Description of the Related Art

Intramedullary rods are commonly used in orthopedic surgery for breaks in the long bones of the extremities, such as the femur and tibia. These rods are used to align and stabilize fractures or breaks of bones and to maintain the bone fragments in their proper alignment relative to each other during the healing process. In addition, intramedullary rods can provide strength to the bone during the convalescence of the patient. One common surgical rod implantation procedure involves drilling the bone marrow canal of the fractured bone from a proximal to a distal end of the bone and inserting an intramedullary rod into this evacuated space. In order to maintain the intramedullary rod in the proper relationship relative to the bone fragments, it is often desirable to insert bone screws or other fasteners through the distal and proximal portions of the intramedullary rod and one or both fragments of the bone. Such a fixation of the rod can make the construct more stable, prevent rotation of the rod within the bone, and prevent longitudinal movement of the bone relative to intramedullary rod.

In order to fix the rod to the bone, intramedullary rods are commonly provided with at least one hole through each of their proximal and distal end portions for receiving screws or fasteners of various configurations. To insert such screws, the objective is to drill holes through the tissue and bone in proper alignment with the holes in the intramedullary rod, and to insert the screws through the holes to lock intramedullary rod in place. Locking the rod near its proximal end (near its point of insertion) is usually accomplished with the help of a jig that helps to locate the proximal hole(s) in the rod. In this proximal region, a relatively short-aimed aiming device can be attached to the jig for reference. A drill can then be passed through the bone and a proximal hole. This technique is relatively straightforward due to the short distance between the accessible proximal end of the rod and the proximal holes in the rod. However, due to the distance between the proximal end of the rod and the point where the holes must be drilled in the bone at the distal end of the rod, it can be difficult to register the drilled hole(s) with the holes in the distal end of the rod. This is particularly true in cases where rod deformation occurred during insertion of the rod into the intramedullary cavity. It can therefore be difficult to successfully align transverse screws with the distal hole(s) for insertion through the bone wall.

Particularly, it is known to those of ordinary skill in the art that an intramedullary rod has a general tendency to bend in the anterior-posterior direction during insertion into the bone, particularly in the femur. The anterior-posterior direction is perpendicular to the axis of the distal rod hole, and thus significantly affects the alignment between the drill-guiding hole in the aiming device and the distal hole in the rod. Medial-lateral bending on the other hand does not significantly affect drill-guiding alignment with the distal hole since the medial-lateral direction is parallel to the axis of the distal hole. Because there is no guarantee that the rod will not bend during insertion, there is always a possibility of misalignment between the distal screw hole and the drill-guiding hole, even assuming perfect alignment between the distal rod hole and the drill-guiding hole prior to nail insertion.

Two primary reasons for failure in distal locking of intramedullary rod to the bone include using an incorrect entry point on the bone and having the wrong orientation of the drill. If either of these two factors exists, the drill may not go through the hole in the rod. An inaccurate entry point also compounds the problem if the rounded end of the drill bit is slightly out of position, thereby weakening the bone and sometimes making it difficult to find a strong point in the bone in which to place the correct drill hole. Inaccurate distal locking can lead to premature failure with breakage of the rod, breakage of the screw, or the breaking of the drill bit within the bone. In addition, if the distal end of the rod is not properly secured, bone misalignment and/or improper healing of the bone may occur.

One known technique for locating a distal hole in an intramedullary rod is with x-ray imaging in combination with a free hand drilling technique. This technique involves watching a fluoroscopic image intensifier to accomplish distal targeting. However, this technique is difficult to use and adds the additional risk of exposing the patient and surgical team to excessive radiation. Even if protective gloves and clothing are utilized, there can still be risks involved with radiation exposure. This can particularly occur in cases where locating the hole(s) in the rod requires multiple attempts. In addition, if the correct alignment of the components is not obtained on the first attempt, multiple perforations of the bone can be required, which can be detrimental to recovery of the patient and the strength of the bone in this area.

Alternative techniques for locating the distal holes in an implanted intramedullary rod have been proposed. However, such methods are often relatively complex and can require additional electronic equipment and visual displays for operation. Such techniques may require special training and/or machine operators, and can be relatively expensive. These techniques can thus be undesirable in the crowded space of a surgical suite, particularly when it is desirable to minimize the amount of equipment and personnel involved in the surgery. Thus, there is a continued need for surgical drilling tools, devices and methods that allow a surgeon to accurately locating the distal holes in an implanted intramedullary rod and for drilling through these holes to allow the rod to be securely fastened to the bone.

SUMMARY OF THE INVENTION

An orthopedic device and method for facilitating the fixation of a distal portion of a device to a bone is provided. In one exemplary embodiment, the orthopedic device and method can facilitate accurate distal fixation of an intramedullary rod within a fractured or damaged bone where the distal fixation area is difficult to locate. Because the devices and methods of the invention do not typically require the use of x-rays or other scanning techniques, the amount of radiation to which the physician is exposed during the distal fixation process is greatly reduced or eliminated. In addition, the process of accurately drilling through the bone and locating corresponding holes in intramedullary rod is much faster than conventional methods that rely primarily on radiation screening and trial-and-error techniques for proper screw placement.

The orthopedic method of the invention may include the use of a bone drill structured for accurately locating the distal holes of an implanted intramedullary rod from within the rod. In particular, such bone drills may drill outwardly from inside intramedullary rod through the thickness of the bone and adjacent tissue. By drilling from inside the rod and using the distal holes to locate the drilling site, the drilled holes are accurately aligned with the distal holes in the rod. This enables the operator to easily and accurately place the screws in their desired locations to fix the distal portion of intramedullary rod to the broken bone.

In one aspect of the present invention, an intramedullary rod structured for positioning within an inner cavity of a bone comprises an elongate body having a proximal end, a distal end, and a channel formed therein, at least one distal hole near the distal end of the elongate body, and locating means formed within the channel of the elongate body. The locating means is structured to allow a surgeon to locate the at least one distal hole with a drilling means from within the channel. The locating means is also structured to support the drilling means when the drilling means is being operated to drill a pilot hole through a bone. Drilling a pilot hole from within an inner cavity of a bone allows the surgeon to determine the angular position of intramedullary rod with respect to the bone.

In one aspect, a method of drilling a hole through an intramedullary rod positioned within a bone comprises inserting an intramedullary rod into a cavity of a bone, positioning a drilling assembly within an inner channel of intramedullary rod, compressing a tissue region with compression means, drilling a pilot hole by advancing a drilling wire or cable from the drilling assembly through an aperture in the intramedullary rod, the pilot hole extending through the bone and adjacent tissue in the compressed tissue region, positioning a pin sleeve over the drill wire or cable, inserting a drill sleeve over the pin sleeve, retracting the drill wire into the drilling assembly, inserting a step pin through the pin sleeve and into the pilot hole, removing the pin sleeve, positioning a cannulated drill bit over the step pin, and drilling a hole through the bone, the hole extending through the aperture in intramedullary rod. Bone screws are then placed in the hole and through the aperture to secure the intramedullary rod to the long bone.

In another aspect of the invention a step pin for locating a pilot hole formed in a bone and for guiding a cannulated drill bit during a surgical procedure is provided. In one aspect, the step pin comprises a first elongate portion having a first diameter, a second elongate portion having a second diameter, the second diameter being less than the first diameter, and a stepped region formed between the first elongate portion and the second elongate portion. The stepped region includes an angled surface structured to provide a gradual transition between the first elongate portion and the second elongate portion. The first elongate portion is structured to be received within an inner channel of a cannulated drill bit so as to guide the cannulated drill bit. The second elongate portion is structured for insertion into a pilot hole extending through a portion of a bone.

In another aspect, the step pin comprises a first elongate portion having an interface means for interfacing with a driving means, wherein the driving means operably rotates the step pin, and a second elongate portion having a generally conical distal tip and a threaded outer surface. The first elongate portion is structured to be received within an inner channel of a cannulated drill bit so as to guide the cannulated drill bit. The second elongate portion is structured to be rotatably driven into a pilot hole extending through a portion of a bone, wherein the threaded outer surface of the second elongate portion provides a secure engagement between the step pin and the bone.

BRIEF DESCRIPTION OF THE DRAWINGS

FIG. 1 is a cross-sectional front view of a fractured femur bone of a human.

FIG. 2 is a cross-sectional front view of the bone of FIG. 1, with an intramedullary rod inserted into an intramedullary cavity of the bone.

FIG. 3A is a side view of one exemplary embodiment of an intramedullary rod.

FIG. 3B is a top view of intramedullary rod of FIG. 3A.

FIG. 5 is a side view of intramedullary rod of FIG. 3A partially in cross-section near a proximal end.

FIG. 6 is a cross-sectional top view of intramedullary rod of FIG. 3A illustrating the internal structure of the rod.

FIG. 13A is a side view of a first alternative embodiment of a step pin in accordance with the invention.

FIG. 13B is a distal end view of the step pin of FIG. 13A.

FIG. 13C is a proximal end view of the step pin of FIG. 13A.

FIG. 14 is a side view of a second alternative embodiment of a step pin in accordance with the invention.

DETAILED DESCRIPTION

Figure 4A:
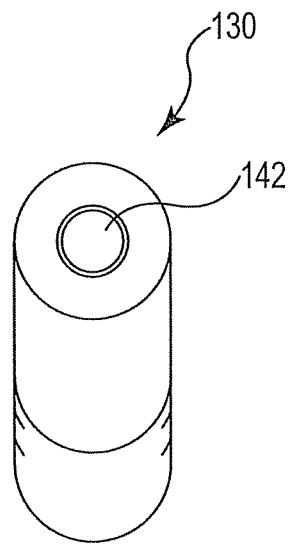
FIG. 4A is a front view of intramedullary rod of FIG. 3A.

FIG. 1 is a cross-sectional view illustrating two portions of a broken femur 100. While the break is generally illustrated as a clean fracture of the bone into two portions, it is possible that the femur could instead be fractured into a number of smaller bone fragments or damaged in some other way. Thus, it should be understood that the devices and methods described herein for two bone pieces can also apply to three or more bone pieces or fragments or even a cracked bone that has not separated into multiple pieces. The femur 100 includes cancellous tissue 104 and an intramedullary cavity 102 that extends along a portion of the length of the femur 100 within the tissue 104. The intramedullary cavity 102 is a generally open area in the femur that is filled or partially filled with bone marrow. In order to prepare a bone such as the femur 100 for insertion of an intramedullary rod therein, the intramedullary cavity 102 can be aspirated and/or lavaged to remove some or all of the marrow and/or loose materials. Optionally, the intramedullary cavity may be reamed to provide a more uniform canal for nail insertion, while also allowing a slightly larger diameter nail to be inserted, thereby providing greater mechanical strength to the system.

FIG. 2 illustrates the femur 100 with its two fractured portions aligned and brought into contact with each other, and an exemplary intramedullary rod 106 inserted within the intramedullary cavity 102. Intramedullary rod 106 includes a bore or channel that runs generally from a proximal end 120 to a distal end 122 of the rod 106. In order to access the intramedullary cavity 102, a hole may be drilled or reamed in the proximal end 108 of the femur 100, through the cortical and cancellous regions and into the proximal portion of the intramedullary canal. Intramedullary rod 106 can then be inserted into the bone through this hole and pushed or hammered downward through the intramedullary cavity 102 toward the distal end 110 of the femur 100. Intramedullary rod 106 can continue to be tamped or pressed downwardly until the distal end 122 of the rod 106 is in its desired position relative to the distal end 110 of the femur 100 and the proximal end 120 of the rod 106 is in its desired position relative to the proximal end 108 of the femur 100.

The above discussion of the insertion of an intramedullary rod into a long bone, such as a femur, is intended as one exemplary procedure for such a rod implantation. A number of alternative procedures can be used as will be appreciated by those of ordinary skill in the art, along with a number of alterative intramedullary rod designs. However, intramedullary rods will generally include a central opening at the proximal end, a bore or channel through the center that runs along at least a portion of the length of the rod, and at least one distal hole spaced from the proximal end, such as near the distal end of the rod. It may also be desirable that intramedullary rod includes at least one proximal screw hole near the proximal end. In such embodiments, it may be further desirable that the proximal and distal holes are spaced from each other by a distance that allows the rod 106 to be sufficiently fixed to the multiple bone segments being repaired.

Now that the general structure and use of an intramedullary rod has been described, one exemplary embodiment of an intramedullary rod will be discussed in detail. FIGS. 3A and 3B are side and top views, respectively, of an exemplary intramedullary rod 130, which generally includes an elongate body 132 having a proximal end 134 and a distal end 136. Intramedullary rod 130 further includes one or more holes disposed near the proximal end 134 and one or more holes disposed near the distal end 136. In the exemplary embodiment of FIGS. 3A and 3B, a first pair of "proximal" holes includes a proximal-proximal hole 138A and a distal-proximal hole 138B, and a second pair of "distal" holes includes a proximal-distal hole 139A and a distal-distal hole 139B. Although two pairs of holes are illustrated, intramedullary rods having any number of such holes are possible. In addition, these holes may be angled in the same or multiple planes, as well as may be slotted to allow dynamic compression or apposition of the fractured segments of the bone.

As illustrated in FIG. 3A, the body 132 of intramedullary rod 130 has a curvature between the proximal end 134 and the distal end 136. The intramedullary rod 130 includes a channel (not shown) therewithin to accommodate a drill assembly that is typically introduced via the proximal end 134. Alternatively, an opening 135 in the side of the intramedullary rod 130 may be used to accommodate a drill assembly. By way of background, a trochanteric intramedullary nail includes a medial-lateral bend in the proximal section and an anterior-posterior bend (which mimics the anatomy of the intramedullary canal of the femur) in the distal section. A trochanteric intramedullary nail is implanted in a patient using a trochanteric insertion portal in the trochanter major to treat fractures of the subtrochanteric and diaphyseal shaft regions of the femur. A piriformis fossa nail is a standard femoral intramedullary nail that utilizes a piriformis fossa portal to treat fractures of the subtrochanteric and diaphyseal shaft regions of the femur. A piriformis fossa nail includes an anterior-posterior bend in the distal section that mimics the anatomy of the intramedullary canal of the femur but does not include a bend in the proximal section of the nail. Thus, as will be appreciated by those of ordinary skill in the art, intramedullary rods may differ in size to be adapted to the long bones of adults and children and may include different curvatures that are adapted for use in different types of bones. Furthermore, intramedullary rods having a body with a curvature in more than one direction, or a substantially straight body with no curvature or bend at all, are contemplated and within the scope of the invention.

Figure 4B:
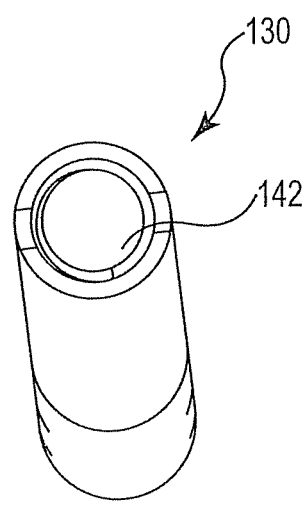
FIG. 4B is a rear view of intramedullary rod of FIG. 3A.

FIGS. 4A and 4B are front and rear views, respectively, of intramedullary rod 130. As illustrated in FIGS. 4A and 4B, intramedullary rod 130 includes a channel 142 extending from the proximal end 134 to the distal end 136. Channel 142 is sized and structured to receive, for example, a drilling assembly for drilling pilot holes through the bone within which intramedullary rod 130 is positioned. Specifically, because intramedullary rods may have the tendency to bend during insertion into a bone, it has been found that the surgeon may account for any bending of intramedullary rod by drilling the pilot holes from the interior of the bone rather than from the exterior of the bone, thereby eliminating rod bending or deformation as a factor in a successful surgical procedure. The benefits of drilling the pilot holes "internally" include improved radial alignment of the rod holes with screws or other fastening means used to anchor the rod to the bone, along with a procedure that is faster and less invasive.

Although channel 142 is particularly suited to receive a drilling assembly therein, numerous other tools may be inserted into the channel 142 such as an obstruction clearing rod or a vacuum tube for removing cancellous tissue or bone marrow from within the channel after intramedullary rod 130 has been inserted into the intramedullary cavity of the bone. Additionally, although intramedullary rod 130 is illustrated as including an open distal end 136 (i.e., the channel 142 extends through the distal end 136), alternative intramedullary rods may be designed with a closed distal end, or may have side channels to allow the drilling assembly to be inserted not from the proximal end, but through this side channel.

FIG. 5 is a side view of intramedullary rod 130 partially in cross-section near the proximal end 134. As illustrated in FIG. 5, the proximal end 134 of intramedullary rod 130 may include an attachment means 144 structured to mate with and engage an external auxiliary component, such as a femoral jig that aids in insertion and alignment of the screws and nails. The exemplary attachment means 144 illustrated in FIG. 5 comprises an internally threaded surface that is structured to mate with an externally threaded surface of the auxiliary component. However, the threaded connection means may be substituted with any suitable means for connection as will be appreciated by those of ordinary skill in the art.

FIG. 6 is a cross-sectional top view of intramedullary rod 130 illustrating the internal structure of the rod. As illustrated in FIG. 6, a first section of the body 132 beginning at the proximal end 134 and extending toward the distal end 136 generally includes a first internal diameter D1. A second section of the body 132 beginning just proximal of the proximal-distal hole 139A and extending to the distal end 136 generally includes a second internal diameter D2 that is less than internal diameter D1. By providing a decrease in the internal diameter of the nail channel at a location just proximal to the distal holes 139A and 139B, the distal end is sized to provide a tight fit for drill assembly such that when the hook is deployed, the drill remains stationary and is not affected by the counterforce of the drill as it encounters bone. Another advantage of the decreased diameter of the rod channel is that it reduces the excess space between the outer surface of the drilling assembly and the inner surface of the rod, thereby limiting radial movement of the drilling assembly. Drilling assemblies for intramedullary rods typically include elongate bodies that are flexible in order to allow the drilling assemblies to be guided into the inner channel of intramedullary rod. Because the elongate body portion of the drilling assembly is thin and flexible, it may vibrate while the internal drill cable is spinning therein. This vibration and movement of the drilling assembly may adversely affect the precision of the pilot hole formed with the drill cable. The decreased diameter of the rod channel 142 near the distal end 136 of intramedullary rod 130 provides increased support for the drilling assembly within the rod channel when the drill is in operation, thereby providing a more precise and accurate pilot hole.

Instead of providing a sudden decrease in the internal diameter of intramedullary rod 130, the internal surface of the rod channel 142 may include a transition surface 146 as illustrated in FIG. 6 that is structured as a "ramp" to gradually guide the drilling assembly into the section of decreased diameter near the distal holes 139A and 139B. In one exemplary embodiment the transition surface may form an angle 143 of about 40 degrees with a center axis of intramedullary rod 130. However, any suitable angle may be used.

Those of ordinary skill in the art will appreciate that the decrease in internal diameter of intramedullary rod 130 may also be provided at the proximal end of rod 130. In addition, including tactile means for the surgeon is also contemplated. For example, providing grooves, bumps or other protrusion or depressions along the internal diameter of the rod channel may provides a tactile or audible means for the surgeon to determine the position of the distal end of the drilling assembly relative to the distal holes. This would allow the surgeon to quickly and easily determine where the distal end of the drilling assembly needs to be positioned in order to align a drilling wire, drill bit or cable of the drilling assembly with the desired distal hole.

Figure 7:
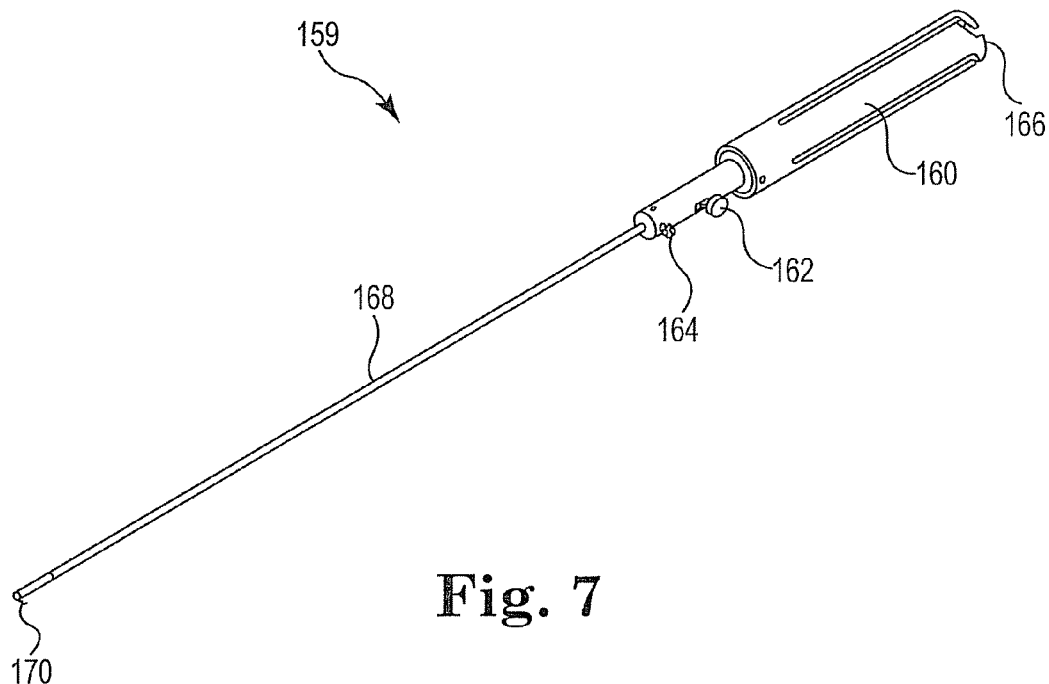
FIG. 7 is a perspective view of a drilling assembly.
Figure 8:
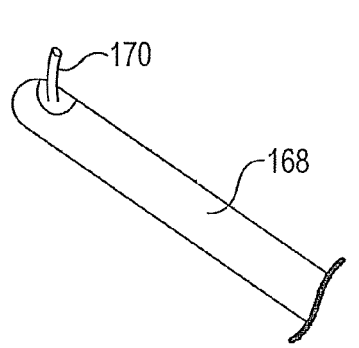
FIG. 8 is a perspective view of a distal end of the drilling assembly of FIG. 7 illustrating a hook member extending therefrom.
Figure 9:
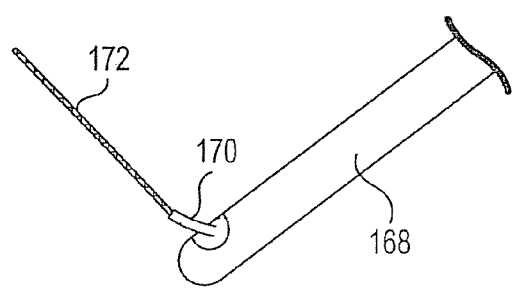
FIG. 9 is a perspective view of the distal end of the drilling assembly of FIG. 7, and further including an extending drill cable.

FIGS. 7-9 illustrate an exemplary drilling assembly 159 that may be used together with intramedullary rod 130. Drilling assembly 159 may generally include a motor guide tube 160, a deployment/retraction button or lever 162, an indexing post 164, a motor attachment component 166, a guide tube 168, a hook 170, and a drilling wire 172. As will be appreciated by those of ordinary skill in the art, drilling wire 172 may take the form of a wire, braided wire, cable, drill bit or any combination of the foregoing. The exemplary drilling wire may be flexible, semi-flexible or rigid depending on its use. As will also be appreciated by those of ordinary skill in the art, a drill motor may be attached to drilling assembly 159 by sliding the drill motor into the motor guide tube 160. The guide tube 168 may be arcuate and retractable for the drilling wire 172. The guide tube 168 allows the drill cable to be deployed inside the limited space of the inner channel of an intramedullary rod during a surgical procedure, such as within the rod channel 142. A large bend radius for the drill cable may help to minimize the stresses on the drilling wire 172. Having a retractable guide tube 168 with drilling wire 172 may also advantageously help to reduce the chances of the drill cable breaking inside a bone during a surgical procedure.

Drilling assembly 159 may include a slotted distance limiter or adaptor from which the lever 162 and indexing post 164 extend, as shown in FIG. 7. As illustrated in FIG. 7, this limiter may be a cylindrical portion that is adjacent to the motor guide tube 160. The deployment/retraction lever 162 may be used for deployment of hook 170 when the distal end of the drilling assembly is positioned adjacent a desired one of the holes in intramedullary rod 130. In the illustrated embodiment, lever 162 includes a post that extends from the surface of the limiter and a cylindrical disk member that extends from the post. The post can further include a spring, a portion with a smaller diameter that is generally positioned on the outside of the limiter, and a portion having a larger diameter that is positioned generally within the limiter. The spring allows movement of the disk member toward and away from the outer surface of the limiter. In order to accommodate the configuration of lever 162, the limiter may include a slot on one side with enlarged portions on each end. In this way, the larger diameter portion of the post can be positioned within the enlarged portions of the slot to lock the hook in either a retracted position when the drilling assembly is being inserted into the rod channel or a deployed position when the surgeon has aligned the distal end of the drilling assembly with the desired hole in intramedullary rod. When it is desired to move the hook to its opposite position, the disk member of lever 162 can be pressed toward the limiter until the larger diameter portion of the post is pressed far enough into the limiter that it disengages from the enlarged portion of the slot. Lever 162 can then be moved along the slot, with the smaller diameter portion of the post sliding within the length of the slot. When lever 162 reaches the opposite end of the slot, the larger diameter portion of the post will be able to move into the enlarged portion of the slot, thereby locking the hook in place. The spring of the post will provide for such a motion. Cams, flip levers, and screw mechanisms, as well as other suitable means may also be used, and are contemplated, as mechanisms for deployment and retraction.

As will be appreciated by those of ordinary skill in the art, the drilling assembly 159 may be operably coupled to a control box for use in controlling the drilling assembly. When in use, the control box can be placed adjacent to but outside a sterile field, such as on a secure stand or table. A hand control device that is operable to manage and control the drilling procedure may also be coupled to the control box. As those of ordinary skill in the art will appreciate, the hand control may include a number of different buttons operable to initiate various commands, such as a start/stop command, a full retract command, a jog forward command, and a jog backward command. Numerous other control commands are also possible.

Figure 10:
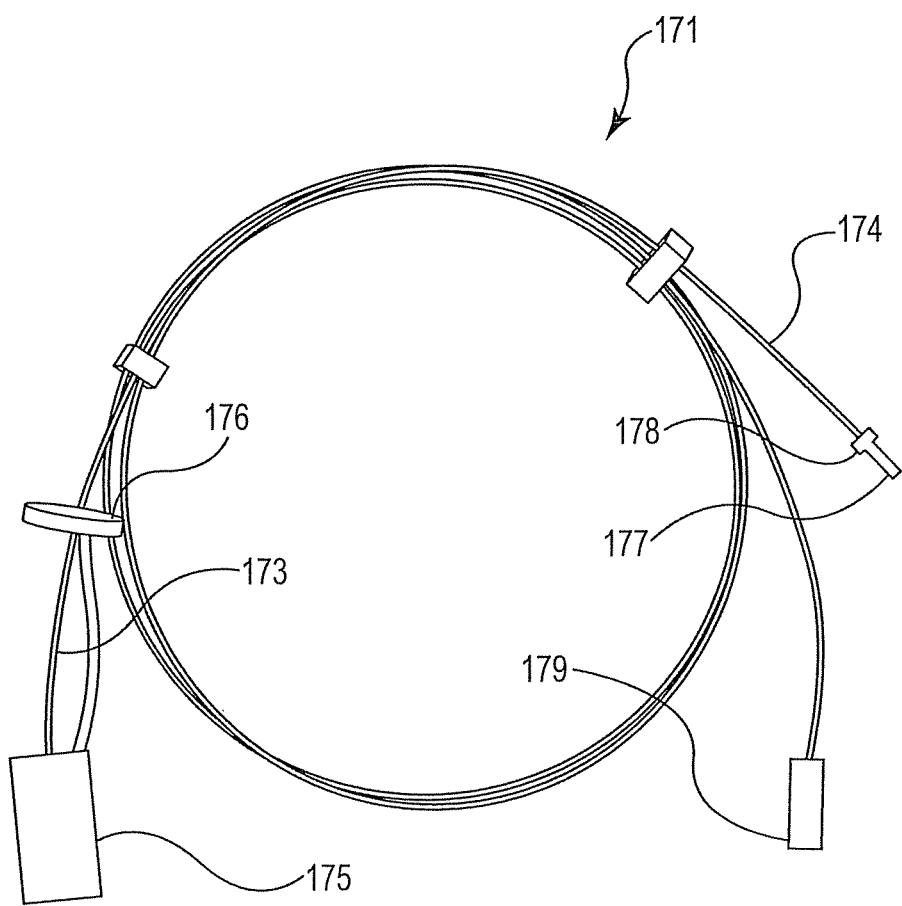
FIG. 10 is a top view of a drill motor assembly.

One exemplary drill motor assembly 171 that is attachable to a control box to control a drilling procedure is illustrated in FIG. 10. As illustrated in FIG. 10, the drill motor assembly may generally include an inner push/pull cable 173, an outer push/pull guide 174, a motor housing 175, a motor guide tube cap 176, an inner control box attachment 177, an outer control box attachment 178, and a drill motor connector 179. Drill motor assembly 171 may include more, less, or different cables, housing, guides, and/or other components, depending on the drill control that is desired for the surgical procedure. The control box may provide means to push or pull the cable, as well as control the overall drilling procedure. In addition, the system may also have means to apply heat or ultrasonics to facilitate the drilling process.

The drill motor assembly 171 is illustrated and described herein as being external to the drilling assembly 159 merely for purposes of example and not limitation. In one exemplary alternative embodiment, one or more of the drill motor assembly components may be reduced in size and placed within the drill "handle," such as the drill motor guide tube 160 of FIG. 7.

Figure 11A:
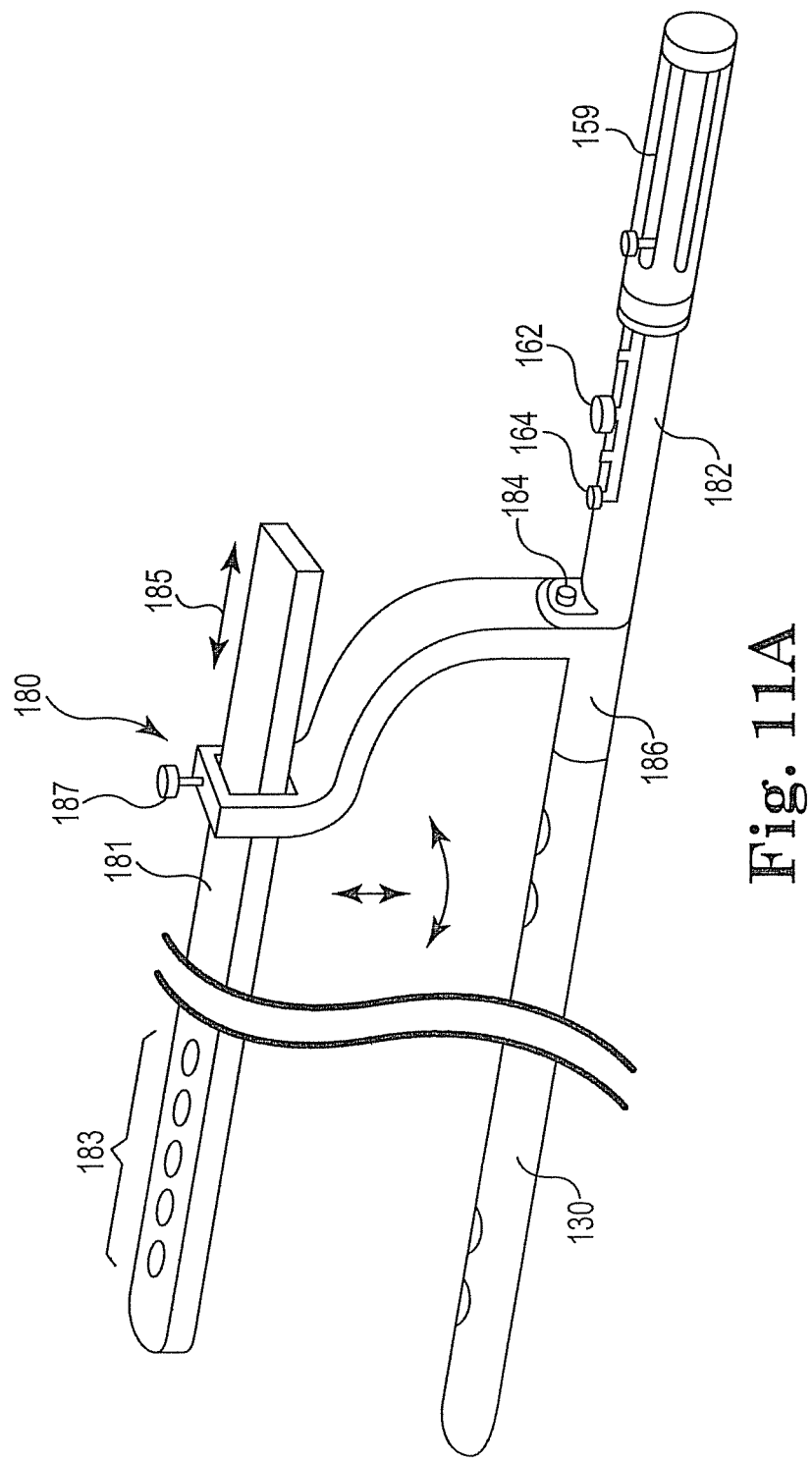
FIG. 11A is a perspective view of a rod interface assembly.

FIG. 11A is a perspective view of one exemplary rod interface assembly 180 which may be coupled to intramedullary rod 130 via the attachment means 144 previously described. As illustrated in FIG. 11A, the rod interface assembly 180 generally includes a jig interface 182, a retention screw 184, and a femoral jig 186. As further illustrated in FIG. 11A, the rod interface assembly 180 may be coupled on a distal end to intramedullary rod 130 and on a proximal end to the drilling assembly 159.

The rod interface assembly 180 may further include an elongated guide arm 181 that is adjustably coupled to the femoral jig 186 to provide an approximation as to the location of the distal holes 139A and 139B in the intramedullary rod 130 upon implantation within a bone. The guide arm 181 may also be used to indicate where the drilling wire 172 will exit the intramedullary rod 130 during a pilot hole drilling procedure. As illustrated in FIG. 11A, the guide arm 181 may include a plurality of apertures 183 that correspond to the location of the distal screw holes in nails of various lengths.

In order to allow the adjustable guide arm 181 to slide back and forth in the direction indicated by arrow 185, an adjustment and locking means 187 is provided at the interface between the femoral jig 186 and the guide arm 181. As illustrated in FIG. 11A, the adjustment and locking means 187 comprises a set screw that may be tightened to engage the guide arm 181 and prevent movement relative to the femoral jig 186. However, any suitable adjustment means may be used including, but not limited to, a ball-and-socket connection, a threaded connection, or a cam engagement connection. These means would allow positioning in multiple planes, positions, and angles.

Figure 11B:
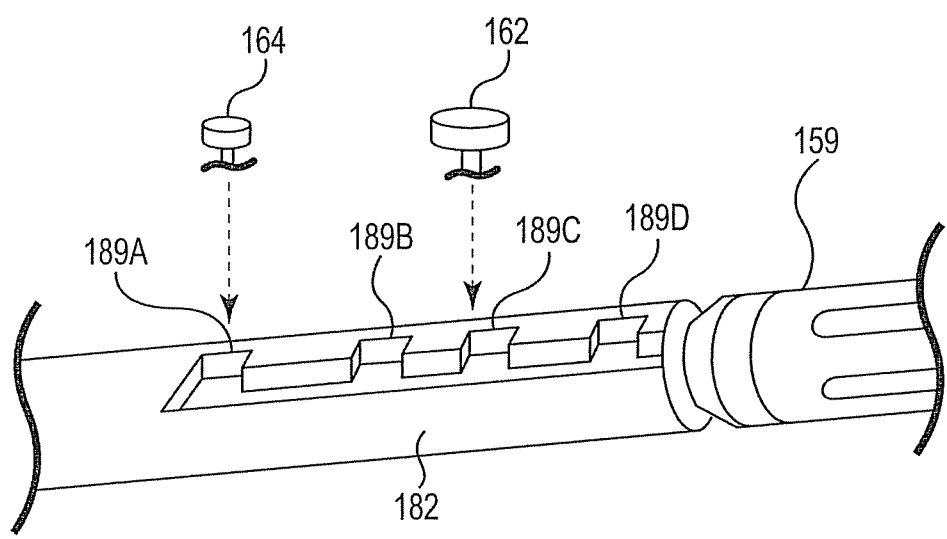
FIG. 11B is an enlarged perspective view of a portion of the rod interface assembly illustrating a screw hole locating means.
Figure 11C:
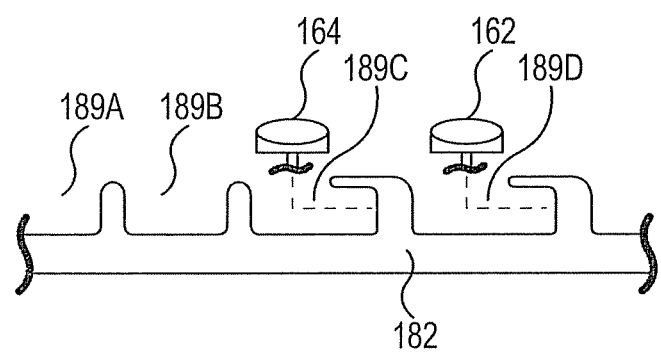
FIG. 11C is a side view of an embodiment portion of the rod interface assembly illustrating a screw hole locating means.

As discussed above, providing a tapered internal diameter or internal surface features such as grooves, bumps, or other protrusions along the internal diameter of the rod channel may provide a tactile means for the surgeon to determine the position of the distal end of the drilling assembly 159 relative to the distal holes 139A and 139B. However, the jig interface 182 may be designed to help guide the placement of the hook 170 of the drilling assembly 159 within the intramedullary rod 130 without the need for such internal tapering or surface features. Particularly, the jig interface 182 may include a track with four slots as illustrated in FIG. 11B and alternative embodiment FIG. 11C including a first slot 189A, a second slot 189B, a third slot 189C, and a fourth slot 189D. For example, when the surgeon desires to drill a pilot hole through the distal-distal hole 139B, the drilling assembly 159 is slid into the jig interface 182 and rotated clockwise so that the indexing post 164 moves into the first slot 189A and the deployment retraction lever 162 is adjacent to the third slot 189C. The hook 170 may then be deployed by pressing the lever 162 in a downward direction and sliding it forward until it pops up in the locked position. Alternatively in the embodiment illustrated in FIG. 11C, the indexing post is positioned into slots 189C and 189D. The hook 170 may then be deployed by pressing the lever 162 in a downward direction and sliding lever 162 forward until locked in the C-shaped slots. With the hook 170 deployed, the surgeon may then drill a pilot hole through the distal-distal hole 139B. In order to locate the proximal-distal hole 139A, the surgeon simply retracts the hook, rotates the drilling assembly 159 counter-clockwise, slides the drilling assembly 159 in the proximal direction, and positions the indexing post 164 in the second slot 189B and the lever 162 adjacent to the fourth slot 189D. A pilot hole through the proximal-distal hole 139A may then be drilled after deploying the hook 170 in the manner previously described.

Figure 12:
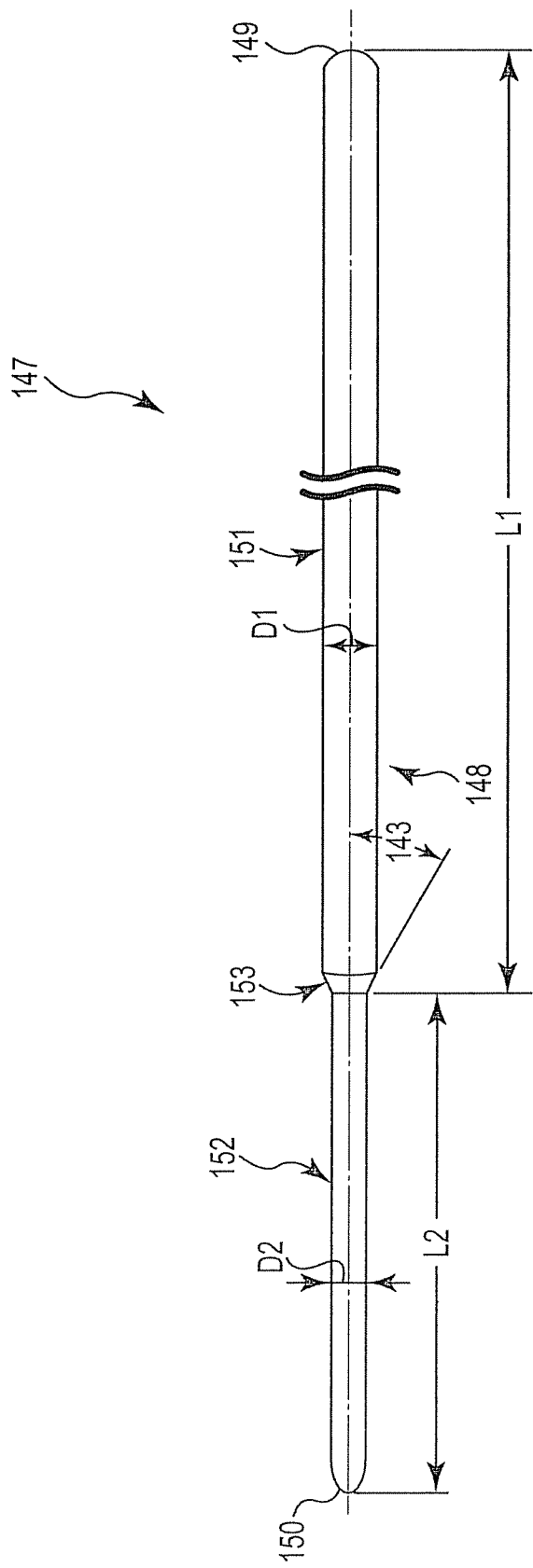
FIG. 12 is a side view of one exemplary embodiment of a step pin in accordance with the invention.
Figure 15:
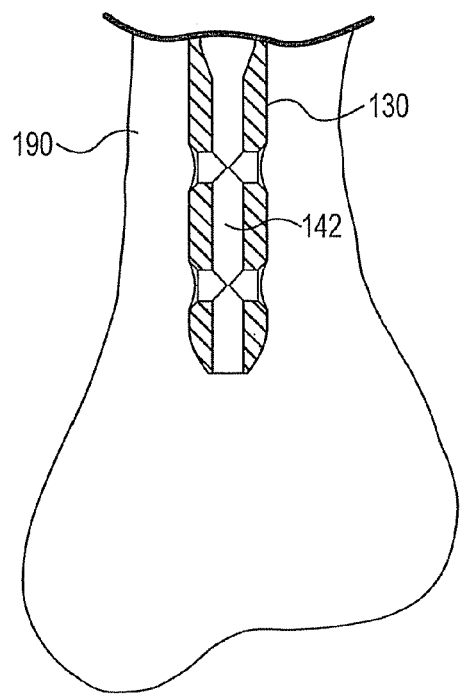
FIGS. 15-23 illustrate the system in accordance with the invention utilized for an exemplary bone drilling operation for placement of an intramedullary rod in a long bone.

FIG. 12 is a side view of an exemplary step pin 147 used in the system and drilling operation in accordance with the invention. As appreciated by those of ordinary skill in the art, a step pin may be used for marking the position of a pilot hole drilled through the bone within which intramedullary rod 130 is positioned. As illustrated in FIG. 12, the step pin 147 may generally include an elongate body 148 having a proximal end 149 and a distal end 150. The body 148 includes a first portion 151 with a diameter D1 and a second portion 152 with a diameter D2 that is less than diameter D1.

The second portion 152 is structured and sized for insertion into the pilot hole in the bone, while the first portion 151 is structured to extend radially outward from the bone along an axis of the pilot hole. Particularly, the diameter D2 of the second portion 152 may be sized relative to the diameter of the pilot hole such that the surgeon may easily slide or "drop" the second portion 152 into the pilot hole. When the second portion 152 is positioned within the pilot hole, the first portion 151 extending radially outward from the bone may function as a guide for a bone drill as will be appreciated by those of ordinary skill in the art. Particularly, a cannulated drill bit of the bone drill may be slid over the exterior surface of the first portion 151 of the step pin 147 such that the first portion 151 serves as a guide through an axis of the pilot hole to allow the cannulated drill bit to drill a larger hole centered substantially about the previously formed pilot hole. Details of this drilling process will be discussed in further detail to follow.

In one exemplary embodiment the diameter D1 may be about 1.1 mm and the diameter D2 may be about 0.7 mm. However, any suitable diameters may be used as will be appreciated by those of ordinary skill in the art. The diameters may depend upon many factors including, but not limited to, the diameter of the pilot hole.

The first and second portions 151 and 152 are separated by a stepped region 153. As illustrated in FIG. 12, the stepped region 153 may include an angled surface that provides a gradual transition between the first portion 151 and the second portion 152 of the body 148. In one exemplary embodiment the transition surface may form an angle 143 of about 30 degrees with a center axis of the step pin 147. However, any suitable angle may be used. For example, the angled surface of the stepped region 153 may alternatively be substantially perpendicular with the center axis of the step pin 147, forming an angle 143 of about 90 degrees.

As will be appreciated by those of ordinary skill in the art, an elongate step pin having a uniform diameter of about 0.7 mm would likely be flexible and pliable even when formed with a stiff metal. Thus, in accordance with the present invention, providing the increased diameter D1 in the first portion 151 improves the overall stiffness of the step pin 147. Providing a stiffer step pin may assist the surgeon in drilling a more precise hole with the cannulated drill bit because the step pin will be less likely to bend or otherwise move during the drilling procedure. In accordance with the present invention, the diameter D1 of the first portion 151 may be sized slightly smaller than the inner diameter of the cannulated drill bit to minimize the excess space between the components while allowing the cannulated drill bit to easily slide along the first portion 151 of the step pin 147.

As illustrated in FIG. 12, the first portion 151 of the body 148 has a length L1 that is greater than a length L2 of the second portion 152. In one exemplary embodiment the length L1 may be about 390 mm and the length L2 may be about 10 mm. However, any suitable lengths may be used as will be appreciated by those of ordinary skill in the art. The length L1 of the first portion 151 is preferably sufficient to enable the surgeon to easily grasp the step pin 147 while inserting the pin into the pilot hole. Furthermore, the desired length L1 may also depend upon the type of bone drill that is used. For instance, one exemplary bone drill is structured such that the step pin may extend longitudinally through both the cannulated drill bit and the body of the bone drill housing and out the proximal end of the bone drill. When this type of bone drill is used, the first portion 151 may preferably have a length sufficient to extend through both the cannulated drill bit and a channel within the bone drill such that the proximal end 149 may be exposed through the proximal end of the bone drill. The length L2 is preferably selected such that the second portion 152 extends at least partially through the near cortex of the bone. In one exemplary embodiment, the length L2 is sufficient to allow the second portion 152 to extend all the way through the near cortex and into the distal hole in intramedullary rod.

FIGS. 13A, 13B, and 13C are side, distal end, and proximal end views, respectively, of one alternative step pin 161 in accordance with the present invention. As illustrated in FIG. 13A, the step pin 161 generally includes an elongate body 163 having a proximal end 165 and a distal end 167. The body 163 includes a first portion 169 and a second portion 171. Similar to the second portion 152 of the step pin 147, the second portion 171 is structured for insertion into the pilot hole in the bone. Similar to the first portion 151 of the step pin 147, the first portion 169 is structured to extend radially outward from the bone along an axis of the pilot hole.

The second portion 171 of the step pin 161 may include a sharp or conically-shaped distal tip 173 structured to assist with locating and inserting the step pin 161 into the pilot hole in the bone. The second portion 171 of the step pin 161 may also have a threaded surface 175 structured to securely couple the step pin 161 within the pilot hole of the bone.

Unlike the step pin 147 previously described, the step pin 161 includes a substantially constant diameter D3 as illustrated in FIG. 13A. The diameter D3 is preferably greater than the diameter of the pilot hole such that the threaded surface 175 of the second portion 171 may be driven into the bone to create a secure engagement between the bone and the step pin 161. An exemplary range for diameter D3 may be about 1.1 mm to about 1.7 mm. However, any suitable diameter may be used as will be appreciated by those of ordinary skill in the art. The diameter may depend upon many factors including, but not limited to, the diameter of the pilot hole.

As illustrated in FIGS. 13A and 13B, the sharp distal tip 173 and the threaded surface 175 may be structured to together form a self-tapping type screw feature on the step pin 161. As appreciated by those of ordinary skill in the art, "self-tapping" generally refers to the ability of a screw or similar device to advance when turned, while at the same time creating its own thread. In one exemplary embodiment as illustrated in FIGS. 13A and 13B, this ability may result from the presence of a gap 177 in the continuity of the threaded surface 175. The edges created by the gap 177 may be structured to cut their own threads in the bone as the threaded surface 175 is driven into the pilot hole. Particularly, the edges adjacent the gap 177 may function by having a cutting surface adapted to remove material as the step pin 161 is driven into the pilot hole, thereby forming an enlarged hole (i.e., with a diameter greater than the pilot hole) for the second portion 171 of the step pin 161.

As illustrated in FIGS. 13A and 13C, the first portion 169 of the step pin 161 may further include an interface means formed thereon that is structured for connection or engagement with a means for driving the step pin 161 into the pilot hole. With reference to FIG. 6C, the exemplary interface means includes three flat surfaces 179 formed on the otherwise tubular first portion 169. As will be appreciated by those of ordinary skill in the art, the three flat surfaces 179 forming the interface means may be structured to engage a standard chuck device on a power drill, such as a "Jacobs chuck." Alternatively, the interface means may be structured for use with a manual driving means, such as a "T-handle" type device. Although the exemplary interface means is illustrated with three flat surfaces 179, it should be understood that a smaller or larger number of flat sides may also be used. Additionally, numerous other designs for an interface means are possible and within the intended scope of the present invention.

As discussed above, the diameter D3 of the step pin 161 is preferably greater than the diameter of the pilot hole within which the step pin 161 is driven. One reason for this "oversizing" is to enable the threaded surface 175 to securely engage with the bone as it is being driven into the pilot hole. Although the first portion 171 is provided with the sharp distal tip 173 that may be used to help locate the pilot hole in the bone, at times the surgeon may find it more difficult to locate the pilot hole with the sharp distal tip 173 as compared to the elongate second portion 152 of the step pin 147 that has a diameter D2 slightly smaller than the diameter of the pilot hole (to allow the second portion 152 to easily slide or drop into the pilot hole). As will be discussed with reference to FIG. 14 below, additional "locating" features may be added to the step pin 161 in order to allow the surgeon to more easily locate the pilot hole.

FIG. 14 is a second alternative embodiment of a step pin 191 in accordance with the present invention. Step pin 191 is similar to the step pin 161 previously described, and similar elements are therefore given similar reference numerals. However, step pin 191 further includes a distal extension 193. The distal extension 193 is similar in structure and function to the second portion 152 of the step pin 147 described above in reference to FIG. 12, and therefore provides means for locating the pilot hole with the distal end of the step pin. Particularly, the distal extension 193 may be sized and structured to slide or drop into the pilot hole, thereby aligning the threaded surface 175 with the pilot hole. Such alignment may allow the step pin 191 to be more easily and accurately threaded into the bone along the axis of the pilot hole. In one exemplary embodiment the distal extension 193 may have a length in a range between about 3 mm and about 10 mm. However, the distal extension 193 may be formed with any suitable length as will be appreciated by those of ordinary skill in the art.

Although step pins in accordance with the present invention may be manufactured using any biocompatible material, one suitable family of materials that is well-suited for biomedical applications is a cobalt-based alloy. One exemplary cobalt-based alloy that is suitable for surgical implant applications is CoCr (ASTM F799). Another family of materials that may be well-suited for biomedical applications is stainless steel. Regardless of the type of material used, the step pin may also be "heat treated" with any suitable heat treatment method, such as annealing or cold working.

Referring now to FIGS. 15-22 an exemplary bone drilling operation using intramedullary rod 130, drilling assembly 159, and step pin 147 in accordance with the system of the invention will be explained In order to prepare the various components described above for use in a drilling operation, a number of exemplary steps can be performed. It should be understood that variations of the order of these steps are contemplated, along with the addition or deletion of steps or processes. Furthermore, the exemplary steps are described with reference to the components of the system previously described merely for purposes of example and not limitation.

Figure 16A:
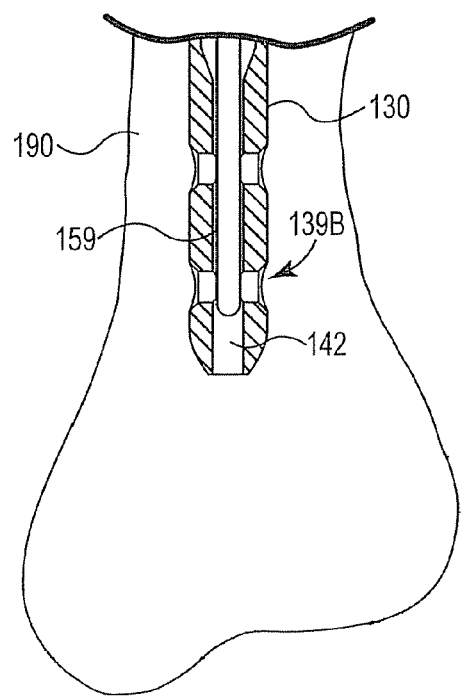

In this exemplary process, the drill motor assembly 171 may be connected to the drilling assembly 159 by placing the motor housing 175 into the motor guide tube 160. The motor guide cap 176 may then be connected to the motor guide tube 160. The next step to prepare for the surgical drilling operation is to attach the femoral jig 186 to intramedullary rod 130, such as with a cannulated bolt. Intramedullary rod 130 is then inserted into the intramedullary cavity of a broken bone 190 as illustrated in FIG. 16A using any suitable insertion means. Jig interface 182 may be attached to the femoral jig 186, such as with the cannulated bolt used to attach the femoral jig 186 to intramedullary rod 130. A suction rod or a vacuum tube may then be inserted into the inner channel 142 of intramedullary rod 130 and attached to a vacuum source to extract extraneous fluids and cancellous debris from the inner channel. Intramedullary rod 130 is now ready for insertion of the drilling assembly 159 so that the drilling operation may begin.

Figure 17:
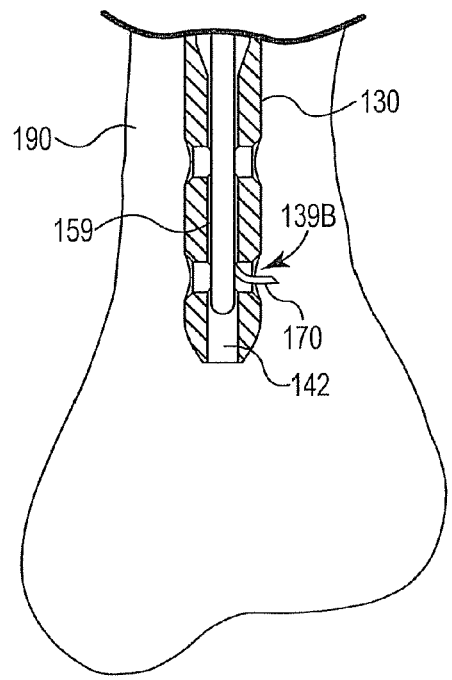

The surgeon may slide the drilling assembly 159 into the channel 142 of intramedullary rod 130 and use the internal structural features of the rod previously discussed to locate the desired one of the distal holes, such as the distal-distal hole 139B as illustrated in FIG. 16A. The hook 170 can then be extended through the distal-distal hole 139B of intramedullary rod 130 as illustrated in FIG. 17 by depressing the appropriate lever on the drilling assembly and sliding it distally. After the hook 170 has been fully deployed from the guide tube 168, the surgeon may begin the actual formation of the pilot hole by drilling through the distal-distal hole 139B.

Figure 16B:
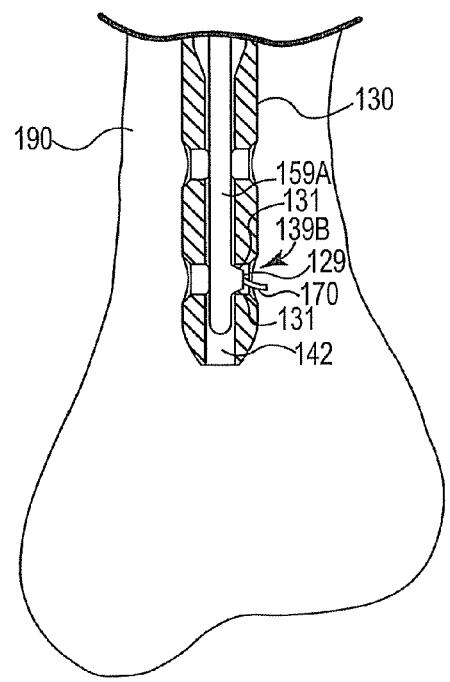
Figure 16C:
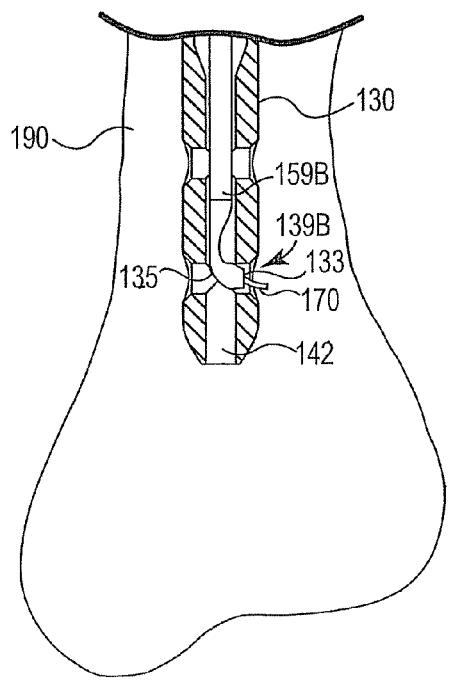
Figure 16D:
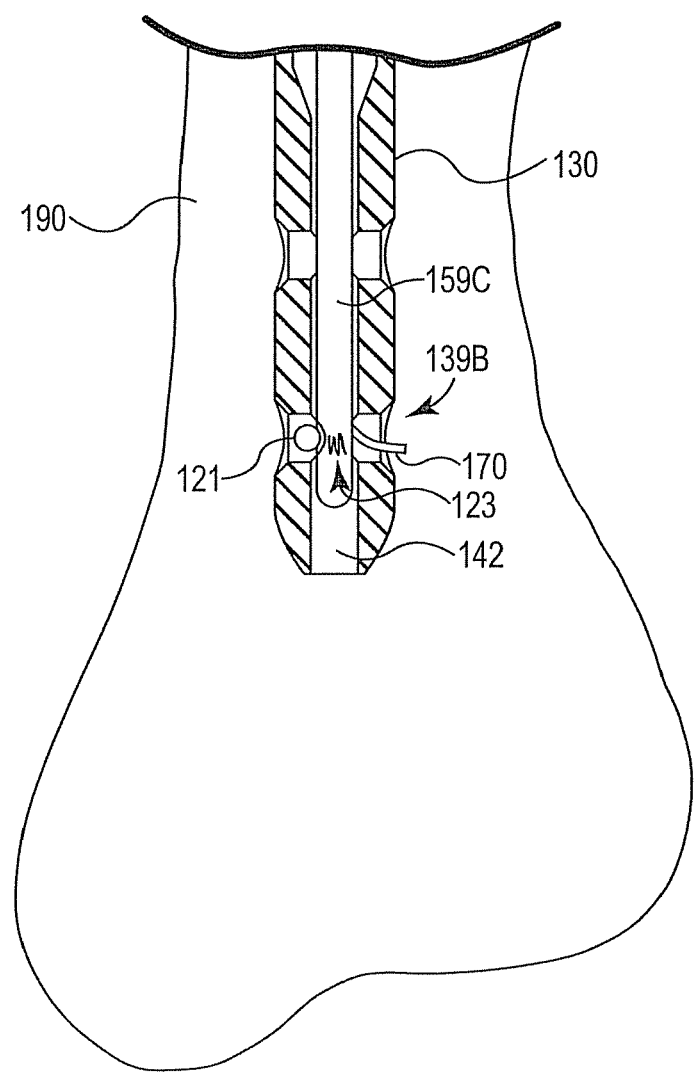
Figure 16E:
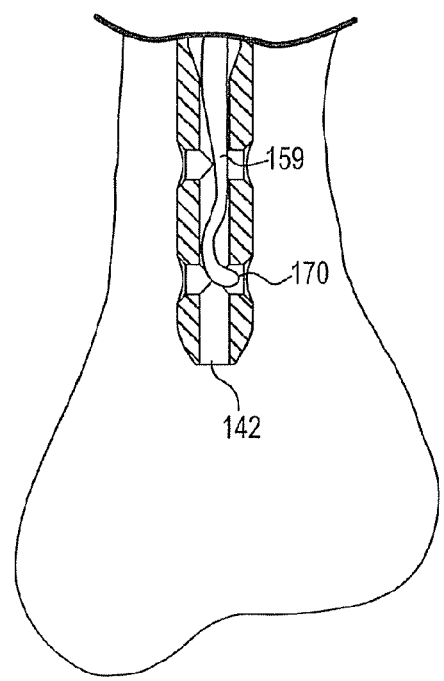
Figure 16F:
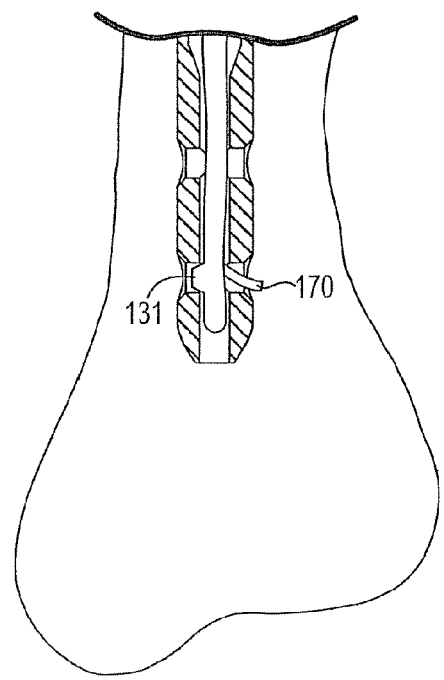

As illustrated in FIGS. 16B-16D, the drilling assembly 159 may further include a distal means to assist the surgeon with locating and/or securing the desired screw hole and maintaining the position of the drilling assembly 159 relative to the screw hole after it is located. Particularly, FIG. 16B is a diagram illustrating one exemplary alternative drilling assembly 159A having a protrusion 129 that is sized and structured to "snap" into the locking screw hole of the intramedullary rod 130. As will be appreciated by those of ordinary skill in the art, the protrusion 129 may be formed from any suitable material, and may be formed integral with or separate from the guide tube 168 of the drilling assembly. As further illustrated in FIG. 16B, the protrusion 129 may include one or more ramped surfaces 131 to assist with the insertion of the protrusion into the locking screw hole and removal of the protrusion from the hole. FIG. 16F illustrates an alternative drilling assembly in which protrusion 131 snaps into the locking screw hole of the intramedullary rod 130 located on the opposition side. As will be appreciate by those of ordinary skill in the art the protrusion 131 can be positioned at a variety of locations on the drilling assembly to snap into any screw hole or other receiving hole located on the intramedullary rod.

FIG. 16C is a diagram illustrating another exemplary alternative drilling assembly 159B having a protrusion 133 similar to the protrusion 129 of FIG. 16B that is sized and structured to "snap" into the locking screw hole of the intramedullary rod 130. However, the protrusion 133 is formed on the distal end of a flexible member 135 extending from the drilling assembly 159B. The flexible member 135 may be shaped generally like the hook 170 contained therein to assist with guiding the hook 170 into the locking screw hole. There may be chamfers along the inside portion of the screw holes to facilitate insertion and removal of the drill assembly with such protrusions. Insertion and removal of the drill assembly to any hole within the nail may be performed either through translation and/or rotation.

FIG. 16D is a diagram illustrating yet another exemplary alternative drilling assembly 159C having a ball detent 121 that is sized and structured to "pop" into the locking screw hole opposite the hole where the hook 170 will be deployed. A coil spring 123 allows for radial movement of the ball detent 121 relative to the drilling assembly 159C and urges the ball detent into the desired locking screw hole when properly aligned. However, the ball detent 121 is also easily removable from the locking screw hole by axial movement of the drilling assembly 159C (either retraction or extension within the rod channel 142). As will be appreciated by those of ordinary skill in the art, any type of surface protrusion may be provided that engages the locking screw hole opposite the hole where the hook 170 will be deployed, such as a protrusion similar to that illustrated in FIG. 16B. An advantage of incorporating a coil spring into the design is the ease of engagement and disengagement with the locking screw hole.

FIG. 16 E illustrates a drilling assembly in which the outer jacket is flexible so that it may be easily positioned within the channel of the intramedullary rod.

Figure 18:
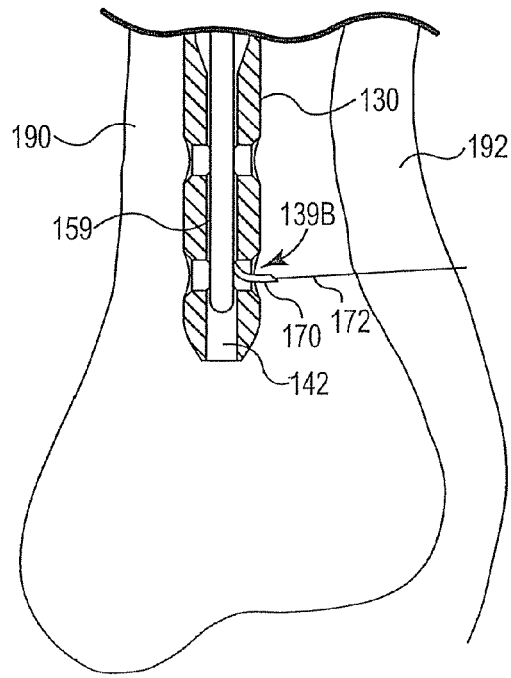
Figure 19A:
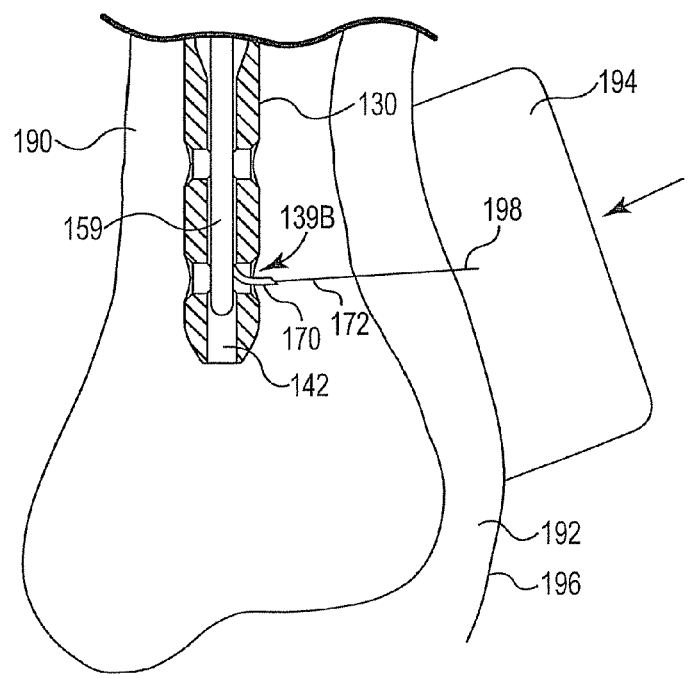

In order to commence formation of the pilot hole through the distal-distal hole 139B, the surgeon may actuate the appropriate control button, such as a start/stop button on a hand controller. The surgeon then monitors the progress of the operation while the rotating drilling wire 172 is advanced radially outward from the distal-distal hole 139B through the bone 190 and the tissue 192 as illustrated in FIG. 18. The surgeon may then actuate the appropriate control button, such as the start/stop button, to stop the drilling operation. Optionally, prior to advancing the drilling wire 172 through the distal-distal hole 139B, the surgeon may first compress the tissue 192 adjacent to where the pilot hole will be formed with a compression means 194 as illustrated in FIG. 19A. As will be appreciated by those of ordinary skill in the art, compressing the tissue 192 in this region may minimize the risk that the elongate, drilling wire 172 will catch the tissue 192 as it is spinning and cause collateral damage to the tissue. One exemplary compression means 194 is a block of semi-rigid foam. One of the benefits of using a foam material is that after the drilling wire 172 reaches the surface of the skin 196, a tip 198 of the drilling wire 172 will puncture the compression means 194 as illustrated in FIG. 19A, signifying to the surgeon that the pilot hole formation is complete. The compression means 194 may then be removed from the surface of the skin 196.

Figure 19B:
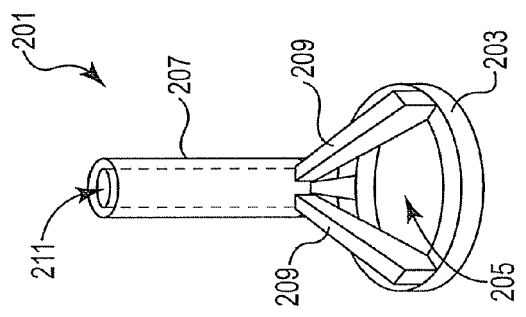
Figure 19C:
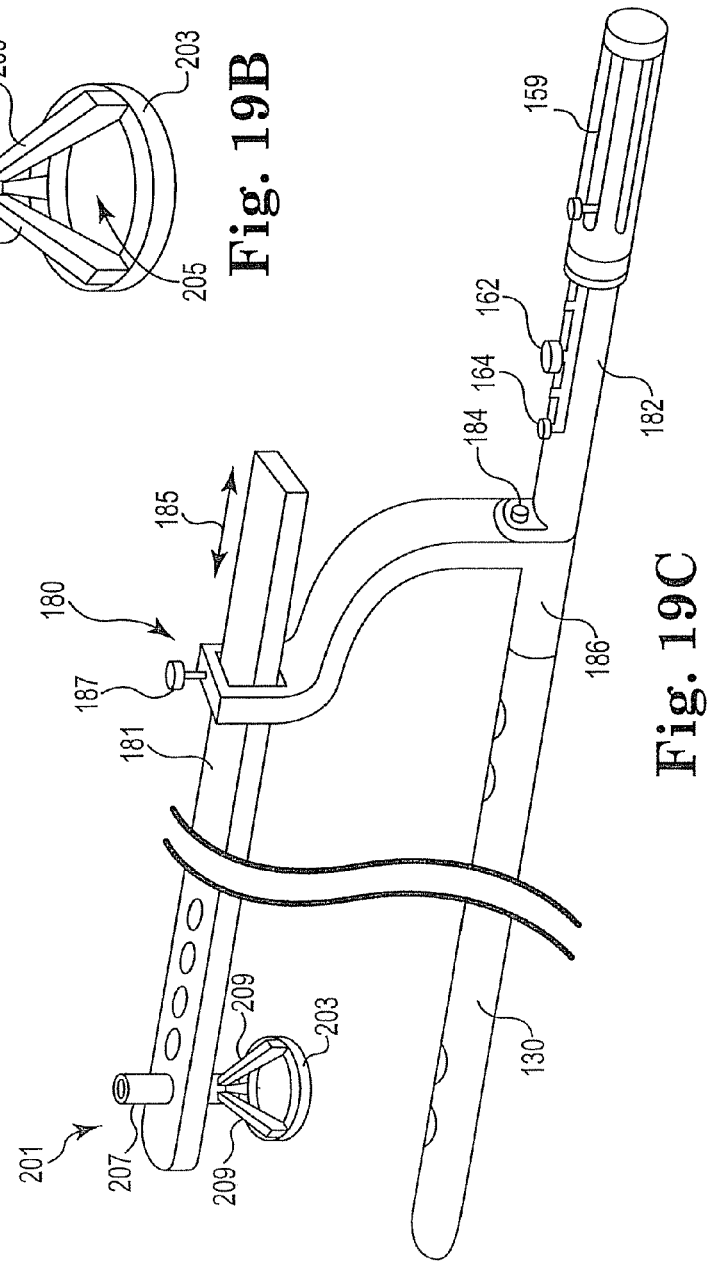

A foam block is illustrated in FIG. 19A merely for purposes of example and not limitation. As will be appreciated by those of ordinary skill in the art, any suitable compression means 194 may be used including, but not limited to, a sterile wrap, a silicone based material, or the like. Additionally, the devices may contain a liquid internally, which when the drilling has penetrated through the skin and into the liquid region of these compression means, would provide the use with a visual indication to stop the drilling, as well as a tactile indication due to the pressure drop form the exiting liquid. Alternatively, a more advanced compression device such as the compression device 201 illustrated in FIG. 19B may be used to provide a desired amount of compression on the tissue 192. Particularly, the compression device 201 of FIG. 19B includes a generally disk-shaped base 203 having an opening 205 therein, a tubular main body 207, and a plurality of struts 209 extending between the base 203 and the main body 207. As will be appreciated by those of ordinary skill in the art, the surgeon may manually grasp the compression device 201, align the opening 205 in the base 203 with the expected exit location of the drilling wire 172, and apply pressure to the base 203 to compress the tissue 192. Alternatively, as illustrated in FIG. 19C, the compression device 201 may be structured for use with the guide arm 181 described above with reference to FIG. 11A. As illustrated in FIG. 19C, the main body 207 of the compression device 201 may be structured for insertion within the apertures 183 of the guide arm 181, and may be removably connected thereto with any suitable connection means as will be appreciated by those skilled in the art. Exemplary connection means may include, but are not limited to, a threaded connection, a ball-and-socket connection, a set screw, clamps, or the like. These connections are not limited to a single dimension or direction, but may allow adjustment and connections of the guide arm in multiple angles or positions.

When the compression device 201 is used in combination with the guide arm 181, the amount of compression applied to the tissue 192 may be adjusted with a compression adjustment means associated with the guide arm 181. In one exemplary embodiment, a ratcheting mechanism may be incorporated into the guide arm 181 for providing step-like increases in the amount of compression applied to the tissue 192. In another exemplary embodiment, the tubular main body 207 of the compression device 201 may be provided with external threads, while the apertures 183 of the guide arm 181 may be provided with corresponding internal threads such that rotation of the main body 207 relative to the guide arm 181 causes movement of the base 203 (and consequently, a controllable amount of compression). In yet another alternative embodiment, a pressure gauge may be provided that is operable to apply a set compression force or a set displacement (which may be selected by the surgeon). Numerous other compression adjustment means are contemplated and within the intended scope of the invention.

Optionally, the opening 205 in the base 203 of the compression device 201 may be covered with a suitable barrier material that provides for more uniform compression of the tissue 192. The barrier material is preferably thin, for example a film, and may be solid or alternatively may include smaller openings, such as a webbing or mesh-like material.

As further illustrated in FIGS. 19B and 19C, the tubular main body 207 of the compression device 201 may include an opening 211 that is sized and structured for receiving various components including the drill sleeve, pin sleeve, drill bit, and/or step pin described below.

Figure 20A:
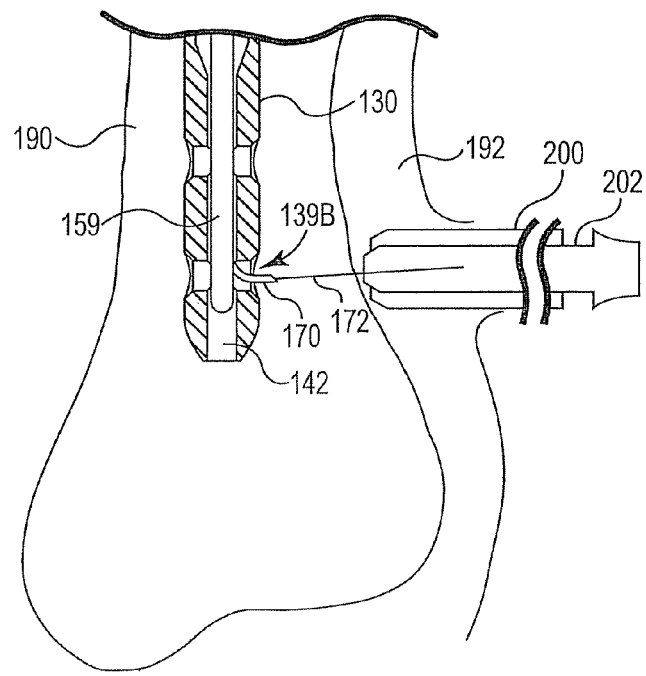

Next, as illustrated in the cross-sectional view of FIG. 20A, the surgeon may create a small incision near the pilot hole in order to locate the drilling wire 172. A series of cannulas with increasing diameters, ratcheting retractors, or any other suitable dilation means known to those of ordinary skill in the art may be used to dilate the incision to increase the surgeon's field of vision while searching for the exit point of the drilling wire 172. Once the drilling wire 172 is located, the surgeon may grasp the tip 198 of the drilling wire and adjust the drilling wire such that it is substantially perpendicular to the corresponding locking screw hole. The surgeon may then insert a drill sleeve 200 over the drilling wire 172. Although not shown, the distal end of the drill sleeve 200, or retraction means, may include "teeth" or other suitable projections for gripping the surface of the bone. With the drill sleeve 200 or other retraction means, in place, the surgeon may adjust the position of the guide arm 181 of the rod interface assembly 180, insert the proximal end of the drill sleeve 200 through one of the apertures 183, and lock the guide arm 181 at the desired position. As will be appreciated by those of ordinary skill in the art, the drill sleeve 200 or other retraction means may be structured to protect the tissue 192 surrounding the newly formed pilot hole to prevent any unintended damage to the tissue during drilling and locking screw placement.

Figure 20B:
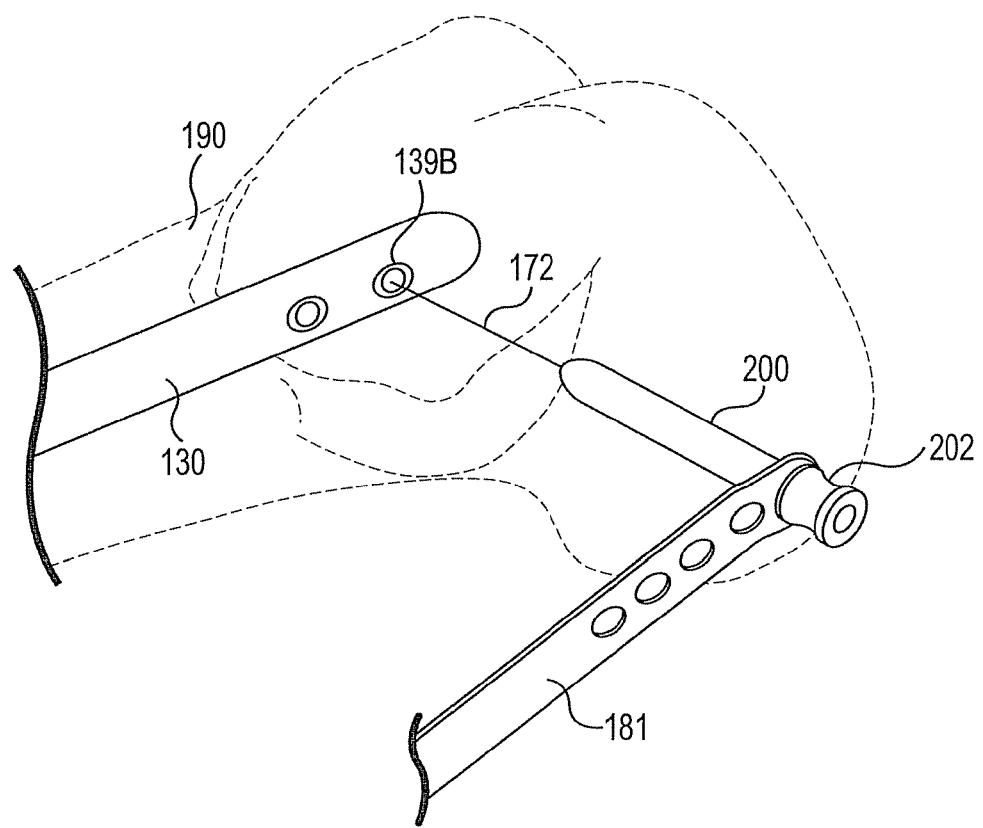

As further illustrated in FIG. 20A, a pin sleeve 202 may also be inserted into the tissue. A perspective view of the drill sleeve 200 and pin sleeve 202 positioned adjacent to the distal-distal hole 139B of intramedullary rod 130 is illustrated in FIG. 20B. The drill and pin sleeves 200 and 202 may either be inserted together (i.e., at the same time) or separately. As will be appreciated by those of ordinary skill in the art, the pin sleeve 202 may be structured to receive and guide the step pin 147. After inserting the drill sleeve 200 and pin sleeve 202 into the tissue 192, the drilling wire 172 may be retracted into the guide body 168, at which time the step pin 147 can be inserted into the pin sleeve 202 and used to locate the pilot hole in the near cortex.

Figure 20C:
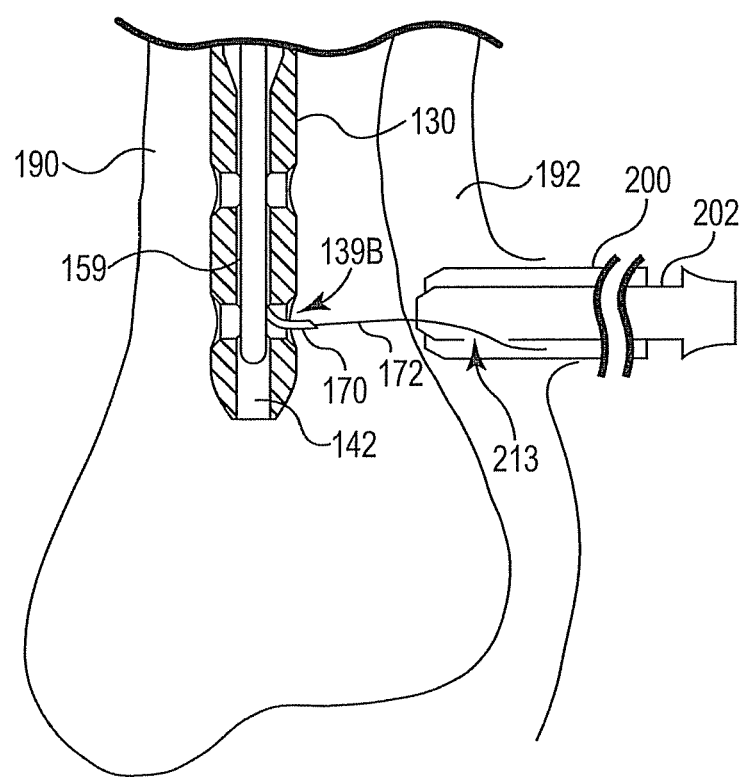

Aligning the step pin 147 with the pilot hole may occasionally prove difficult, even with the assistance of the pin sleeve 202. Thus, in one exemplary alternative embodiment as illustrated in FIG. 20C, the pin sleeve 202 may include a window 213 in the side wall that allows for passage of the distal end of the drilling wire 172. Particularly, the wire 172 may be pulled through the window 213 of the pin sleeve 202 to assist with alignment of the pin sleeve 202 with the location on the bone where the pilot hole was formed. Once the pin sleeve 202 is properly aligned, the step pin 147 may be inserted into the pin sleeve 202 and the drilling wire 172 retracted.

Figure 21A:
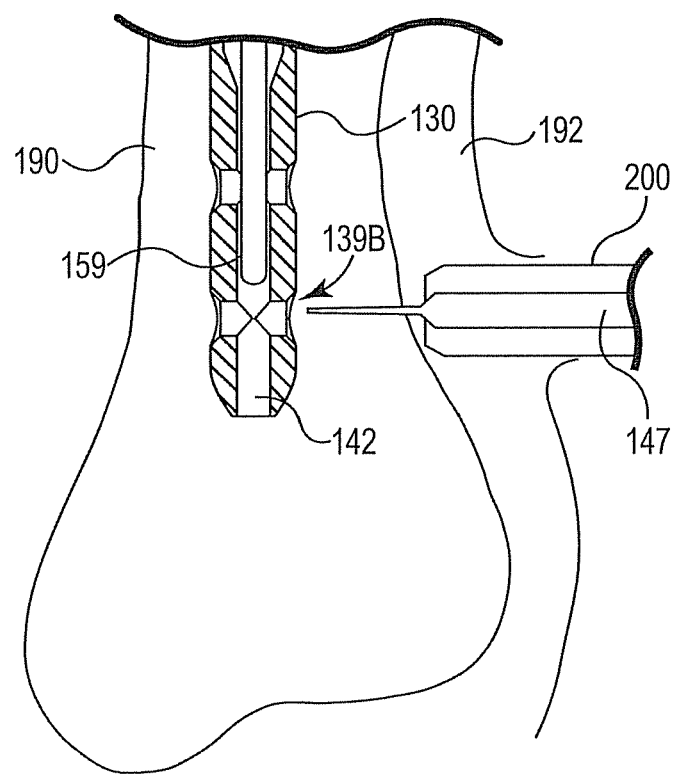
Figure 21B:
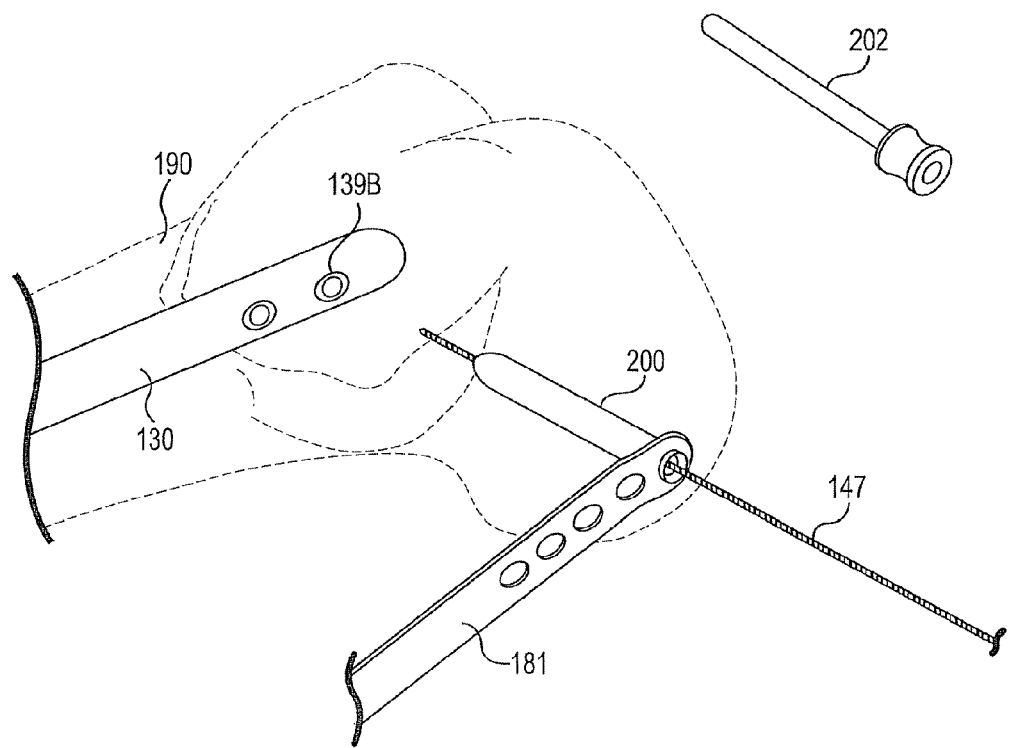

After the step pin 147 is inserted into the pilot hole, the hook 170 can be retracted and the drilling assembly 159 can be pulled proximally by a small distance to allow drilling through to the far cortex. With reference to the exemplary drilling assembly 159, the hook 170 may be retracted by depressing the plunger on the deployment/retraction lever 162 and sliding the plunger proximally within the slot with a slight force until the hook is fully retracted. The pin sleeve 202 may also be removed from the tissue 192 as illustrated in the cross-sectional view of FIG. 21A, leaving only the drill sleeve 200 and step pin 147 in the tissue. A perspective view of the step pin 147 extending through the drill sleeve 200 (with the pin sleeve 202 removed) and into the pilot hole is illustrated in FIG. 21B.

Figure 22A:
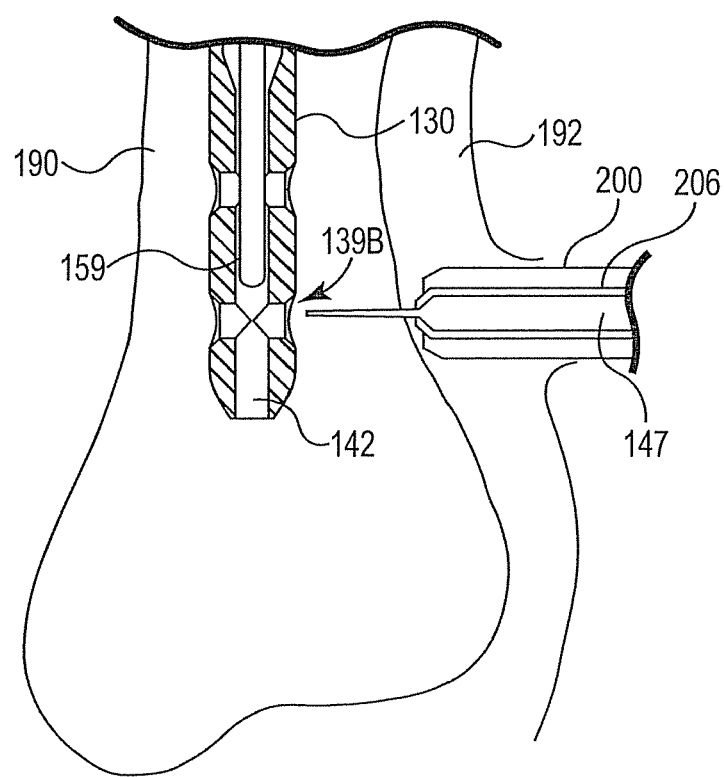
Figure 22B:
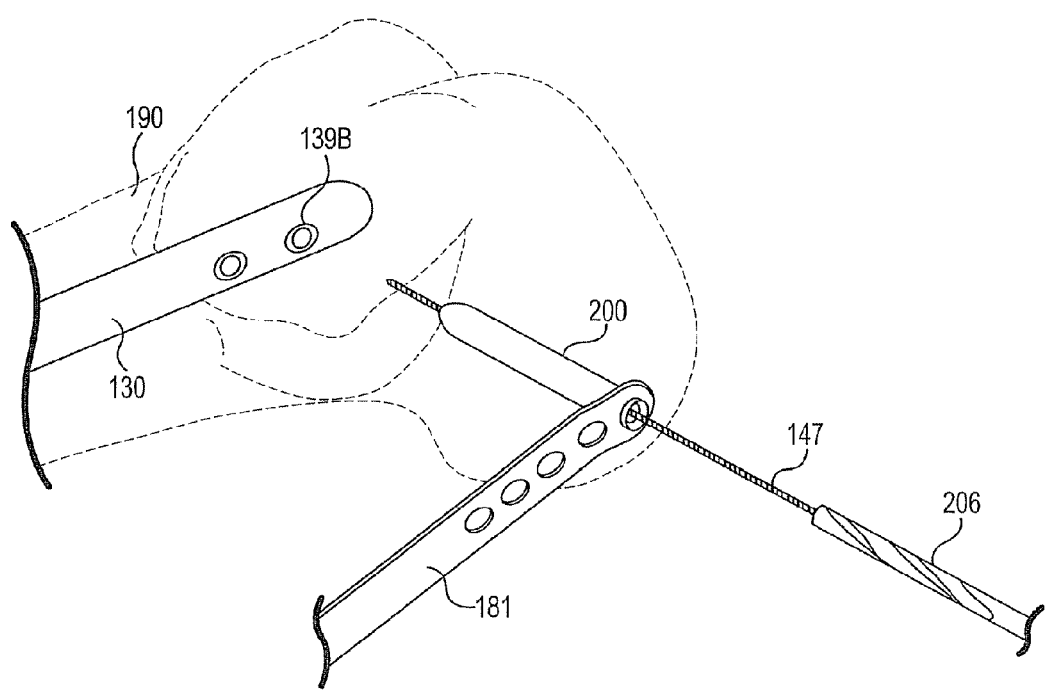

As illustrated in the cross-sectional and perspective views of FIGS. 22A and 22B, respectively, a cannulated drill bit 206 may then be slid over the step pin 147. A separate drill that is not associated with the drilling assembly 159 can then be used to completely penetrate through the first cortical wall of the bone 190. The drill can then be stopped and the cannulated drill bit 206 can be advanced until the second cortical wall of the bone 190 is reached. Optionally, in order to confirm the proper placement of the cannulated drill bit 206, the drilling assembly 159 in intramedullary rod 130 may be moved distally within the channel 142 until the surgeon can feel the distal end of the drilling assembly touch the cannulated drill bit 206. The drilling assembly 159 may then be retracted to its previous position, and the drill coupled to the cannulated drill bit 206 may then be used to penetrate the second cortical wall. To reduce the possibility of unintended tissue damage, it may be desirable to carefully monitor and limit the distance that the cannulated drill bit 206 extends beyond the second cortical wall.

After drilling through the second cortical wall of the bone 190, the cannulated drill bit 206, step pin 147, and drill sleeve 200 may be removed to expose the bi-cortical hole. A depth gauge may then be used to measure for the appropriate length of locking screw, using conventional methods, and an appropriately sized locking screw may then be inserted into the distal-distal hole 139B in order to fasten intramedullary rod 130 in place.

A similar procedure to the one described with reference to the distal-distal hole 139B may be used for drilling through the proximal-distal hole 139A.

It should be understood that variations of the order of the steps described above with reference to FIGS. 15-22 are contemplated, along with the addition or deletion of steps or processes. Furthermore, the bone drilling process and method of using a step pin were described with reference to intramedullary rod 130, the drilling assembly 159, and the step pin 147 merely for purposes of example and not limitation. Thus, alternative intramedullary rods, drilling assemblies, and step pins may also be used, such as the alternative step pins 161 and 191 described above.

Figure 23:
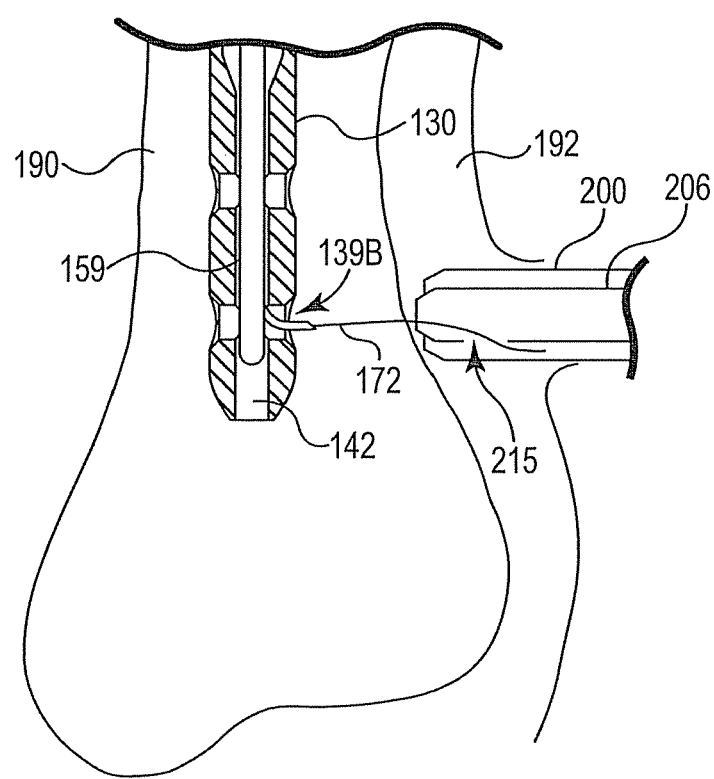

Additionally, as will be appreciated by those of ordinary skill in the art, it may be possible to drill through the cortical walls of the bone 190 without using a step pin for guidance. For example, the cannulated drill bit 206 may include a window 215 in the side wall that allows for passage of the distal end of the drilling wire 172 in a manner similar to that previously described with reference to the window 213 in the pin sleeve 202. Particularly, after placement of the drill sleeve 200 in the incision, the cannulated drill bit 206 may be inserted into the drill sleeve 200 and the drilling wire 172 pulled through the window 215 to align the drill bit 206 with the pilot hole location. Once the cannulated drill bit 206 has been properly aligned, the drilling wire 172 may be retracted and the holes in the cortical walls drilled as discussed above. Thus, as will be obvious to those of ordinary skill in the art, use of a drill bit with a window such as that illustrated in FIG. 23 may eliminate the need for a step pin altogether.

Although the present invention has been described with reference to preferred embodiments, workers skilled in the art will recognize that changes may be made in form and detail without departing from the spirit and scope of the invention.

What is claimed:

1. A drill assembly for drilling a hole through a bone comprising:
    an intramedullary rod comprising an elongate body defining a channel therewithin and including at least one screw hole extending from said lumen to an outer surface of said elongate body; said screw hole having chamfered side walls;
    a drill guide tube structured to receive a drill cable, said drill guide tube comprising a proximal end, a distal end, a length extending between the proximal and distal ends, an outer surface having a fixed shape extending along the length of the guide tube between the promixal and distal ends, and a protrusion extending from the outer surface, said drill guide tube structured to be introduced into said intramedullary rod channel, said protrusion being integrally formed with said drill guide tube and having chamfered side walls that join a base whose length is greater than the length of a tip thereof, said protrusion chamfered side walls configured to engagingly mate with said chamfered side walls of said at least one screw hole to locate said screw hole and maintain the position of said drill cable relative to said screw hole.

2. The drill assembly of claim 1 wherein said intramedullary rod includes at least a first screw hole and second screw hole in apposition to said first screw hole.

3. The drill assembly of claim 2 wherein said protrusion is positioned on said guide tube to mate with said second screw hole.

4. The drill assembly of claim 1 wherein said intramedullary rod includes a plurality of screw holes and said protrusion is positioned on said guide tube to mate with one or more of said plurality of screw holes.

5. The drill assembly of claim 1 wherein said guide tube is flexible.

6. The drill assembly of claim 1, wherein the drill guide tube comprises a single-piece construction.

7. A drill assembly for drilling a hole through a bone comprising:
    an intramedullary rod comprising an elongate body defining a channel therewithin and including at least one screw hole extending from said channel to an outer surface of said elongate body, said screw hole having chamfered side walls;
    a drill guide tube structured to receive a drill cable, said drill guide tube including a flexible end piece thereon, said flexible end piece having a bulbous distal end with chamfered side walls, said drill guide tube structured to be introduced into said intramedullary rod channel, and said chamfered side walls of the bulbous distal end configured to engagingly mate with said chamfered side walls of said at least one screw hole to locate said screw hole and maintain the position of said drill cable relative to said screw hole; and
    a hook that is extendible and retractable from a distal end surface of the bulbous distal end of the flexible end piece.

8. The drill assembly of claim 7 wherein said intramedullary rod includes at least a first screw hole and second screw hole opposite to said first screw hole.

* * * * *

UNITED STATES PATENT AND TRADEMARK OFFICE
CERTIFICATE OF CORRECTION

PATENT NO. : 9,526,540 B2
APPLICATION NO. : 13/505137
DATED : December 27, 2016
INVENTOR(S) : Patrick R. Corneille et al.

Page 1 of 1

It is certified that error appears in the above-identified patent and that said Letters Patent is hereby corrected as shown below:

In the Claims

Claim 1,
Column 18, Line 3, "Lumen" should be --channel--

Claim 1,
Column 18, Line 12, immediately following "the outer surface" please insert --proximal to the distal end of the drill tube--

Signed and Sealed this
Ninth Day of May, 2017

Michelle K. Lee
*Director of the United States Patent and Trademark Office*